(12) United States Patent
Kay

(10) Patent No.: US 7,563,025 B2
(45) Date of Patent: Jul. 21, 2009

(54) METHODS AND APPARATUS FOR PRESERVING ORIENTATION INFORMATION IN RADIOGRAPHY IMAGES

(76) Inventor: George W. Kay, 146 Billings St., Sharon, MA (US) 02067

( * ) Notice: Subject to any disclaimer, the term of this patent is extended or adjusted under 35 U.S.C. 154(b) by 3 days.

(21) Appl. No.: 11/279,891

(22) Filed: Apr. 15, 2006

(65) Prior Publication Data

US 2007/0081631 A1  Apr. 12, 2007

Related U.S. Application Data

(63) Continuation-in-part of application No. 10/510,967, filed as application No. PCT/US03/11267 on Apr. 14, 2003, now Pat. No. 7,140,769, which is a continuation of application No. 10/392,158, filed on Mar. 18, 2003.

(60) Provisional application No. 60/431,282, filed on Dec. 6, 2002, provisional application No. 60/372,323, filed on Apr. 12, 2002.

(51) Int. Cl.
*A61B 6/14* (2006.01)
(52) U.S. Cl. .......................... 378/168; 378/165; 378/38
(58) Field of Classification Search ............. 378/38–40, 378/162–165, 167–170
See application file for complete search history.

(56) References Cited

U.S. PATENT DOCUMENTS

| 2,426,286 | A | 8/1947 | Stadler ........................ 378/165 |
|---|---|---|---|
| 4,356,398 | A | 10/1982 | Komaki et al. ............... 250/582 |
| 4,578,581 | A | 3/1986 | Tanaka et al. ............... 250/587 |
| 4,598,207 | A | 7/1986 | Naruse et al. ............. 250/484.4 |
| 4,625,325 | A | 11/1986 | Beraudo ...................... 378/168 |
| 4,803,359 | A | 2/1989 | Hosoi et al. .................. 250/586 |
| 4,814,616 | A | 3/1989 | Saotome ...................... 250/586 |
| 4,829,548 | A | 5/1989 | Halm et al. ................... 378/38 |
| 4,835,398 | A | 5/1989 | Nakamura ............... 250/484.4 |
| 4,933,558 | A | 6/1990 | Carter et al. ................ 250/582 |
| 4,965,455 | A | 10/1990 | Schneider et al. ......... 250/484.4 |
| 5,077,778 | A * | 12/1991 | Fabian ........................ 378/162 |
| 5,123,040 | A | 6/1992 | Fabian ........................ 378/182 |
| 5,434,418 | A | 7/1995 | Schick .................. 250/370.11 |
| 5,696,805 | A | 12/1997 | Gaborski et al. .............. 378/54 |
| 6,042,267 | A | 3/2000 | Muraki et al. ............... 378/169 |
| 6,055,326 | A | 4/2000 | Chang et al. ................ 382/132 |
| 6,174,330 | B1 | 1/2001 | Stinson ..................... 623/1.34 |
| 6,255,667 | B1 | 7/2001 | Rantanen ..................... 250/585 |

(Continued)

OTHER PUBLICATIONS

Digora Intra-Oral Imaging Systems by Soredex, brochure, May 2001.

(Continued)

*Primary Examiner*—Courtney Thomas
(74) *Attorney, Agent, or Firm*—Lowrie, Lando & Anastasi, LLP

(57) ABSTRACT

A method for preserving orientation information in an image may comprise: collecting image data, including orientation information inherent to collecting the image data; and embedding in the image data an orientation mark unambiguously identifying when the image data is presented in a correct viewing orientation. Image data is stored in a medium together with data forming an embedded orientation mark which is bilaterally asymmetrical in at least two orthogonal axes. In a variation, the data forming the embedded orientation mark further comprises at least one humanly recognizable text or punctuation character, word or trademark.

13 Claims, 20 Drawing Sheets

U.S. PATENT DOCUMENTS 6,303,101 B1     10/2001     Klaveness et al. ............ 424/9.1
6,542,579 B1*     4/2003     Takasawa ................... 378/165

OTHER PUBLICATIONS

D.A.Miles, DDS,MS, FRCD, Understanding Digital Radiography, posted on Internet by dentalproducts.net Originally published in Dec. 2000 Dental Practice Report, http://www.dentalproducts.net/sml/0012/miles0012/miles0012a.asp, Apr. 27, 2002.

Fujifilm Products, Fuji Computed Radiography, http://home.fujifilm.com/info/products/inform/fuji_radio.html, Apr. 27, 2002.

Agfa, Radview Phosphor Scanner, http://ndt.agfa.com/bu/ndt/index.nsf/EN/computedradiography.htm, Apr. 27, 2002.

A/T ScanX™ Digital Imaging System PN73400, Operator's Manual, 2002.

X-Ray Mass Attenuation Coefficients—BISMUTH, 3 pp., http://physics.nist.gov/PhysRefData/XrayMassCoef/ElemTab/z83.html, Dec. 14, 2002.

Digora Fmx—Soredex, Technical data, http://www.soredex.com/digora_fmx_data.shtml, Nov. 21, 2002, p. 1 of 2.

Terry, B.R., DMD et al., Digital Radiography, http://www.rootcanalspecialist.com/digitalradiography.htm, Apr. 27, 2002, p. 1 of 2.

Digora Fmx—Soredex, Technical data, Aug. 2002.

Digora Intra-Oral Imaging Systems by Soredex, http://webspace.dialnet.com/preseli.computers_pcs/Digora.htm, Nov. 21, 2002.

Digora Optime Chairside Digital Imaging Plate System, Digora_optime_lores.pdf, Mar. 2005.

* cited by examiner

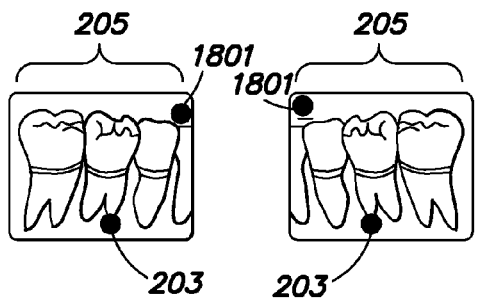 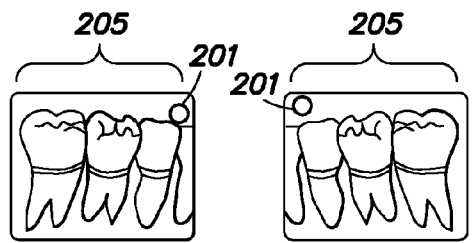
FIG. 22  FIG. 23        FIG. 24  FIG. 25
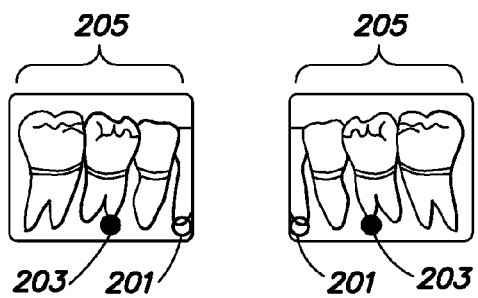 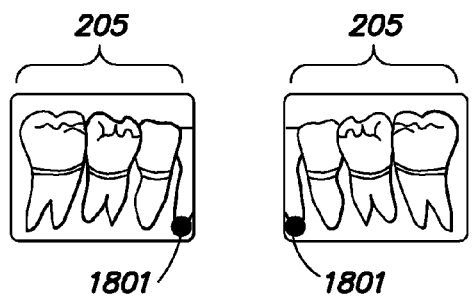
FIG. 26  FIG. 27        FIG. 28  FIG. 29
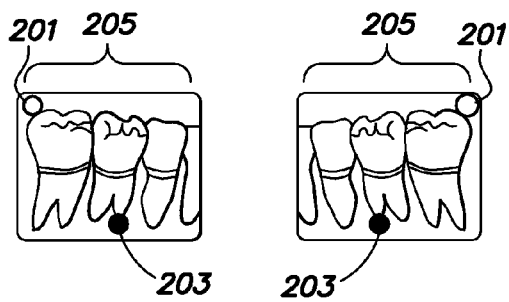 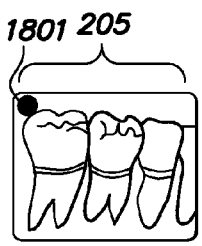 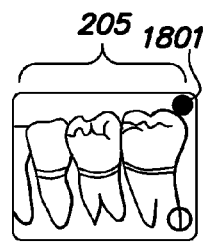
FIG. 30  FIG. 31        FIG. 32  FIG. 33

METHODS AND APPARATUS FOR PRESERVING ORIENTATION INFORMATION IN RADIOGRAPHY IMAGES

CROSS REFERENCE TO RELATED APPLICATION

This application is a continuation in part of U.S. patent application Ser. No. 10/510,967, entitled "A RADIATION SENSITIVE RECORDING PLATE AND METHOD OF MAKING AND USING SAME," filed Oct. 12, 2004, which is a National Phase filing under 35 U.S.C. § 371 of International Application PCT/US03/11267, entitled "A RADIATION SENSITIVE RECORDING PLATE AND METHOD OF MAKING AND USING SAME," filed Apr. 14, 2003, which claims priority to U.S. patent application Ser. No. 10/392,158, entitled "A RADIATION SENSITIVE RECORDING PLATE AND METHOD OF MAKING AND USING SAME," filed on Mar. 18, 2003, to U.S. Provisional Application Ser. No. 60/372,323, entitled "METHOD FOR INTERNALLY LABELING THE ORIENTATION OF EXPOSURE OF RADIATION-SENSITIVE PLATES BY PRODUCING A RECOGNIZABLE PATTERN WITHIN THE INFORMATION SET PRODUCED BY SUCH EXPOSURE," filed on Apr. 12, 2002, and to U.S. Provisional Patent Application Ser. No. 60/431,282, entitled "A RADIATION SENSITIVE RECORDING PLATE, A METHOD OF MAKING SAME AND A METHOD OF RECORDING AND ORIENTING IMAGES," filed on Dec. 6, 2002, all of which are herein incorporated by reference in their entirety.

BACKGROUND

This application relates generally to image processing. More specifically, the application relates to identifying image orientation. Yet more specifically, the application relates to identifying image orientation in medical and dental X-ray shadow-grams.

Images produced in conventional roll-film cameras, on film, are easy to orient correctly because the camera is constructed in such a way that the emulsion of the film always faces the lens. Because of the shapes of film cassettes and cameras, the film cannot be inserted in modern cameras with the emulsion facing away from the lens, so it is always known that the light, or other radiation recorded by the film, struck the film from the emulsion side. Thus, when orienting slides for projection, or film images for viewing on a light box, it is always known to put the emulsion toward the projection lens in the slide projector, or to put the film on the light box with the emulsion towards the viewer. When that is done, the image seen by the viewer, whether projected or viewed on the light box, will have a known defined correspondence with the orientation of the objects in the original scene. Moreover, even if orientation is lost, reorienting based on determining where the emulsion is will reestablish proper orientation.

Likewise, digital images produced using cameras with detectors such as charge-coupled devices (CCDs), complementary metal oxide semiconductor (CMOS), thin film transistor (TFT) and others that are sensitive to exposure from one side only are inherently unambiguous in their original form. The cameras used to produce such images are physically constructed and arranged with a lens or lens mount in a fixed position relative to the detector, so that the direction from which the exposing radiation strikes the detector is always known. CCD and CMOS sensors used in dental digital or direct radiography also are physically constructed and arranged to produce a diagnostic image only when exposed from the proper direction. Such CCD and CMOS sensors include a radiopaque element on the side away from the intended direction of exposure. Laterality of the images may however be reversed by the use of software used to process, display, and them.

The problem is somewhat more complicated for dental or medical diagnostic images produced on conventional film. One common type of dental or medical diagnostic image is a shadow-gram produced by placing a radiographic film on one side of the object to be imaged and a source of radiation to which the film is sensitive on a diametrically opposite side of the object to be imaged. The radiation, for example X-radiation, casts a shadow of the object to be imaged on the film, thus revealing density variations within the object whose shadow has been cast. When a standard orientation of the examined object is used, and the film is viewed from the same side as the radiation source exposing the emulsion, the laterality, i.e. right versus left, of the object is preserved, because the viewer can unambiguously discern right from left side by observing the image alone. However, medical or dental X-ray film can be exposed and viewed from either side because the film is transparent to both X-rays and visible light. To further complicate matters of orientation, an emulsion is often applied to both sides of the film in order to lower the dosage of radiation required to produce the diagnostic image, by increasing the sensitivity of the film. However, film thus constructed cannot be oriented on the basis of which side has an emulsion. Thus, it is desirable to identify from which side the film was exposed to radiation and so indicate the side from which it should be viewed.

Conventionally, and due in part to its high sensitivity to visible light, as well as to X-rays, radiographic film is usually held in an opaque cassette which not only prevents exposure to visible light, but also limits X-ray exposure to one side of the film, only. The side of the cassette through which large format film, such as that used for medical X-ray applications, is exposed often includes radiopaque labels indicating various patient information, including patient name, date of exposure, side of the patient (e.g., left or right arm), etc., for example, which provide a clear indication embedded in the image of the side of the film from which the exposure was made. If such labels are used, reversal of the image by viewing from the side opposite the side of exposing incident rays also causes the label characters to reverse, clearly indicating the reversed orientation of the diagnostic image. Systems also exist (e.g., Planmeca's pantomograph) which incorporate within the film cassette a mechanism which automatically optically imprints on the margin of the film, and therefore the image, pertinent patient, exposure, and orientation data during the exposure of the film. Often physical features, e.g., notches in the edge or corner of the film or keyways that orient the cassette itself to a cassette holder within the apparatus exposing the object, are used to further ensure that a consistent orientation of the film in the cassette and the exposure apparatus, and thus, the relative orientation of film and the image recorded on it to the object, is obtained and retrievable independently of the structure represented in the diagnostic image itself. The "back side" of the cassette is itself at least partially radiopaque over its entire surface, so as to prevent accidental exposure from the wrong side. The spatial orientation of the original form creating the shadow in the image is thus clearly and unambiguously defined. However, this clear and unambiguous outcome relies either upon the mechanical features noted above, or upon the X-ray radiology technician properly loading the cassette and placing the orienting labels, followed by exposing from the correct side. Otherwise, if the positioning of the film or the cassette is improper, the image produced visually reflects the improper orientation and the process and must be repeated.

Some conventional radiographic film cassettes are fitted on each side of the film with intensifying screens which are covered with a layer of fluorescent phosphor. These phosphors, when exposed to X-rays, fluoresce with visible light which is capable of exposing the film contained within the cassette thereby intensifying the X-ray image signal recorded in the emulsion. Since the emulsion is more sensitive to visible light than to X-ray irradiation, and since it is exposed to the fluorescent light from both sides of the film, the latent image recorded is primarily a result of this indirect exposure by visible light rather than by the X-ray photons that have traversed the imaged tissues.

Unlike the large format films described above, dental intraoral films are conventionally provided prepackaged in packets, which may be disposable and which are often flexible. Because intraoral films must be small enough to be positioned within the mouth, there is little room available for the types of labels described above. In the case of conventional silver halide dental intraoral films, proper orientation is identified by a raised or embossed bump on the film and packet that points away from a radiopaque backing in the packet that prevents or limits inadvertent exposure from the wrong side. The bump, which projects from the plane of the film in the direction from which the shadow is cast, is a permanent feature of the film and persists as marker of the orientation in the dimension perpendicular to the plane of the film, providing a method by which the viewer can identify the side of exposure. If an exposure is made from the wrong side, the resulting image is recognizably undiagnostic because of its degradation caused by the radiopaque backing contained within the packet. The radiopaque backing, typically a textured heavy metal foil, causes exposure from the wrong side to appear in the image as a textured pattern, while the embossed feature preserves and identifies the orientation information for the viewer. As with medical X-rays in which a proper outcome is assured by correct loading of the cassette, a proper outcome using intraoral dental films is assured only by correct assembly of the packet at the factory, followed by correct handling by the radiology technician. The degradation of the image evidencing improper exposure orientation of the film, which results in the reversal of the diagnostic image when the bump feature is used to orient the image, is, however, immediately obvious to the viewer, assuring that mistaken identification of features in the image is highly unlikely and traceable. This combination of an orientation feature and a feature preventing exposure from the wrong side is now conventional.

By convention, dental intraoral films are produced in a variety of generally rectangular standard sizes, with rounded corners. Also by convention, when prepared for viewing, they are grouped in an anatomical arrangement in a holder called a mount. Standard mounts hold films in one of two orientations only: with the longer dimension of the film in a horizontal orientation, henceforth in this application referred to as "landscape" orientation; and with the longer dimension of the film oriented vertically, henceforth referred to in this application as "portrait" orientation.

In keeping with conventions of viewing of radiographic images, on film or on a computer monitor, and for nonambiguity and clarity of the descriptions, the frame of reference for principal directions is based on the image plane, itself. Up shall be a direction generally from any point in the image toward a top of the edge of the image, while down is in an opposite direction. With the up direction oriented in a natural fashion for a viewer, left and right correspond to the viewer's left and right. Vertical corresponds to the direction of a line running up and down from any point in the image.

U.S. Pat. No. 4,625,325 describes a method which incorporates both conventional radiographic film and phosphor in the same process with radiopaque material. The device described patented therein includes a film packet, similar to the intraoral dental film packet described above. The device also incorporates a pocket for holding a plate which is inserted by the radiology technician prior to the exposure of the film. The plate, which is coated with a phosphor on the side facing the film and radiation source and which incorporates radiopaque material on the opposite side, is positioned adjacent to the film in the packet. The plate is an image amplifier similar to the intensifying screens used in cassettes described earlier. During the exposure, the film is exposed both by X-rays impinging directly on the film and by the phosphorescence emitted by the plate phosphor stimulated by the same X-rays. Those X-rays which have passed both the film and the phosphor are absorbed by the radiopaque backing, thereby limiting tissue exposure downstream of the recording surfaces. The packet, film and plate are held by a jig in a position such that the film and plate can only be exposed from one side. The phosphor only functions as an amplifier to provide improved signal-to-noise ratio and to lower the radiation dose per exposure. The phosphor film does not function as a storage phosphor holding a latent image, and is not scanned to produce a diagnostic digital image. Furthermore, no issues of image orientation ambiguity from a digital electronic image result from the process, because the image is recorded on conventional radiographic film, as before.

Conventional Phosphor Plate Technology

Radiosensitive phosphor storage plates, hereafter sometimes referred to in this application as PSPs, have recently started displacing conventional radiographic emulsion film for recording medical and dental images. Advantages including superior sensitivity, lack of dependence on toxic chemical processing fluids, relative insensitivity to ambient light, reusability, and the ease of digital data storage and transmission all stimulate the growth of this technology. The image orientation issues noted above with respect to conventional film; however, as well as new image orientation problems, for example resulting from the use of image processing software, manifest themselves in the use of PSPs. As discussed above, the orientation of the image produced by film technology was identified unambiguously by the presence of a three-dimensional object, namely the bump protruding from the film surface toward the object casting the shadow, providing a permanent and absolute reference in a dimension perpendicular to the plane of the film. The other two dimensions, superior-inferior and anterior-posterior are inferred from the anatomical structures in the image. Unlike the image incorporated into a three-dimensional physical object, i.e., the film with a bump, the images produced by existing PSP technologies are stored and displayed as two-dimensional views without a complete, definite, and permanent indicator of the direction of exposure or of viewing. Incomplete references or markers, as discussed below are incorporated into the existing systems; however, none of the systems are unambiguous, permanent, or complete by virtue of their design.

Although the radiosensitive PSPs are sensitive to a specific, diagnostic radiation type, e.g., X-rays, they are substantially insensitive to visible light for the purposes of registering an image. They can be handled in ordinary room light, absent the usual cassette until the time of the exposure. They are, for sanitary and other purposes such as reducing wear and tear on the phosphor, inserted into radiolucent plastic film sleeves before each use. The PSPs are also reusable to produce multiple images over a period of time. Erasure, by prolonged exposure to intense visible light, and repackaging in the disposable radiolucent plastic film sleeves is done by a radiology technician at the point of use, rather than at the point of manufacture.

A scanner, through laser illumination, stimulates the phosphor to emit light in an amount which depends on the amount of prior exposure to X-rays, and which in turn is registered as data signal. Currently, commercially available phosphor-based digital radiology systems use PSPs having a polymer sheet substrate supporting a pastel-colored phosphor layer applied to one surface of the substrate. The other surface of the substrate appears black. For the purpose of this application, the side of the plate which is intended by the manufacturer as the preferred side to be read, e.g., by the scanner, to produce the diagnostic image shall be referred to as the "front side", while the opposite side of the plate and sensitive layer shall be referred to as the "back side" henceforth. For practical reasons related to the current technology, the side of the plate that is generally intended as the side to be scanned ("front side") is also the side on which the sensitive layer is nearer the surface of the plate and is visible, thereby available for excitation by the scanning mechanism. "Front" and "back" should not, however, be taken to mean correct, incorrect, preferred or the like.

Even though the sensitive layer, e.g., phosphor, is available for scanning from one side, the "front side", only, it can be exposed and register a latent image from either side, and in some commercial systems equally well. As a result of the possibility that the shadow recorded by the sensitive layer, e.g., phosphor, could have been cast from either side of the plane of the plate, the recorded latent image as well as the visible image resulting from its scan are ambiguous with respect to their laterality. Thus, when recording bilaterally symmetric structures, e.g., left or right jaw, mirror images result, which can be easily confused since they are not uniquely oriented. Therefore, the two sides of the body (or mouth) can be confused by the viewer of the image, resulting in erroneous diagnosis and/or treatment. As a result, current commercially available PSP systems for dental use, such as those produced by Air Techniques Inc. and Gendex™, provide on each plate detailed explicit instructions to package and expose PSPs in a specific orientation, so as to preserve image orientation.

Some dental PSP systems employ techniques analogous with technology used in conventional emulsion film. For example, Digora® (available from Soredex), system incorporate a slightly radiopaque layer on the "back side" of the plate, which reduces patient irradiation by rays that pass through the plate and into the patient. The radiopacity of the backing is featureless, but the backing degrades an image exposed by irradiation from the "back side."

The conventional Digora® Optime PSP includes a "marker" that produces a visible mark in the image if the imaging plate is exposed "the wrong way around," according to promotional material produced by the Digora® Optime maker, Soredex, GE Healthcare Finland Oy. Significantly, the mark produced in the image by the "marker" of this conventional technology only indicates that the image was produced by radiation rays that pass from the target to be imaged, to the plate, through the back side of the plate, which Soredex considers to be the "wrong" side of the plate. In such a case, if the user knows that the image has not been corrected, i.e. mirrored through a vertical line, then such mirroring can be performed in the viewing software; however, a corrected image that was exposed through the back of the plate is indistinguishable on the basis of the mark from an uncorrected image that was also exposed through the back of the plate. It is still possible for the user to confuse which structure is imaged in a particular image using this conventional system.

Systems such as Scan-X™ (available from Air Techniques Inc.) and Denoptics™ (available from Gendex) each feature a distinctive marker. The markers are distinctively shaped, either a lower case letter "a" opaquely printed over the "front side" of the phosphor or a small open circle evident as an absence of the phosphor in a localized area, respectively. These markers, referred to as front side markers, are incorporated at the time of fabrication of the PSPs by the manufacturer and are constructed in such a way as to always be read from the phosphor by the scanner in a constant fashion independent of any exposure variables. The result of the presence of a marker produced by either of the above variants, i.e. Scan-X and Denoptics, in fabrication is a diminution, or absence, of phosphorescence from the area of the plate so altered, during scanning. This relative lack of signal is reflected in the visible scan image as a distinct shape, i.e., mark, corresponding to the shape and the location of the marker on the PSP.

Any features of such a front side marker that are either asymmetric or placed asymmetrically with respect to a vertical axis of symmetry of the plate, or both, become represented by similarly asymmetric features of a front side mark in the image of the plate following a scan. Furthermore, this mark becomes detectably reversed with respect to its laterality either in respect to its asymmetric location or its internal asymmetry as a result of software horizontal reflection of the scanned image, or both when both exist. As the placement of the source of the radiation during the exposure has no influence over the appearance of the image of such a front side mark, this front side mark is well suited as an indicator of any reversal of laterality of the entire image following the completion of the scan.

For practical reasons, namely because the image produced by each of the commercially available PSP technology systems can be displayed and viewed in one of four orientations only, which orientations correspond to the conventional orientations for emulsion-based radiographic film mounts, and which orientations are separated by steps of ninety degree rotation relative one another, the rotational transformations of the image (and the plate position) in this application will also be confined to ninety degree steps, or multiples thereof. Thus the available set of orientations to consider for any image will be the two "landscape" and two "portrait" possibilities, i.e., one right side up and one up side down for each category.

The configuration shown in FIG. 1 illustrates generally how a dental X-ray plate can be used to produce images, X-ray shadowgrams, of a patient's lower jaw and teeth. The particular physiological structure is illustrative of the symmetry problem discussed above. However, the problem occurs in connection with many physiological structures as a result of the inherent symmetry present in most biological systems, particularly humans and animals. The configuration of FIG. 1 is now described as it relates to conventional dental X-ray PSPs. Later, in the DETAILED DESCRIPTION, the configuration of FIG. 1 is referenced as it relates to aspects of the invention, which may be practiced in this configuration, as well as other suitable configurations.

For purposes of illustration a human anatomical structure will be used as an example of the issues of laterality preservation in radiographic imaging of paired or bilaterally symmetric structures. The anatomical structure illustrated in FIG.

1 is a human lower jaw, i.e., a human mandible 101, having a set of teeth 102 set therein. Although not shown, for clarity, it may be assumed that the mandible 101 and teeth 102 are part of a living patient's body, covered with the soft tissues, etc. This particular patient has a diagnostically significant condition, e.g., an abscess, denoted by filled circle 103. A radiology technician, physician, dentist or other has placed a conventional dental PSP 104 in the patient's mouth in a position suitable for capturing a shadowgram of three of the patient's posterior teeth 105 on either side of the patient's mouth. Although in actual practice, the plate 104 would be placed close to the teeth whose shadowgram is being recorded, so as to produce a clear image, for the convenience of illustration the plate 104 is shown centered between the teeth of the left side and the teeth of the right side of the patient's mouth. Finally, two alternative locations for X-ray sources, SOURCE L and SOURCE R, are shown. X-ray source, SOURCE R, produces the images shown in FIGS. 2 and 3, while X-ray source, SOURCE L, produces the images shown in FIGS. 4 and 5. FIGS. 2, 3, 4 and 5 are now described, with reference back to FIG. 1, as required.

FIGS. 2, 3, 4 and 5 illustrate four images that can be produced using a conventional PSP exposed from each of two sides, using each of two differently located sources, e.g., positioned at SOURCE L and SOURCE R. Because the reference conventional commercial plate has an open circle mark on the "front side" of the plate, in one corner, an open circle 201 appears in each of the images. Images produced by source, SOURCE L, include images 205 of posterior teeth 105 and images produced by source, SOURCE R, include both images 205 of posterior teeth 105 and an image 203 of diagnostically significant condition 103. In conventional PSP usage, the open circle is present on the "front side" of the plate and is intended to direct the radiology technician, physician, dentist or other to face that side of the plate toward the exposure source. However, such a consistent usage is not guaranteed.

If the plate were to be consistently exposed from only one side (e.g., "front side"), then a front side mark produced by a front side marker would provide an absolute reference of laterality by eliminating confusion introduced by horizontally flipping of the image. Such reflection results in the displacement in the image of the open circle front side mark from the lower right or the upper left corners of the image to the lower left or the upper right in the images which are in "landscape" orientation. The displacement would be the reverse for "portrait" orientation. Although recommended, and consistent with best practice, such a consistent exposure of the intraoral plate from the sensitive side is not guaranteed either in the loading of the plate into the sleeve or in its placement during exposure itself. (Medical large format PSP systems generally use cassettes which not only hold the plate in desired orientation during exposure but also are loaded and unloaded by the scanner itself during the scanning process. This method of plate handling prevents inadvertent reversal of laterality prior to the creation of the viewable image.)

It should be noted that certain predictable rules of translocation govern a system composed of a radiographic plate, the image it holds, the long and the short axes of symmetry of the plate or its image, and a universe of combinations of two motions, a reflection through a vertical plane perpendicular to that of the image and a 90 degree rotation around an axis perpendicular to the plane of the plate at the intersection of its long and short axes of symmetry.

The reflection of the image within this system can occur through one of two modes. The first mode involves casting the shadow, i.e., registering the image, onto the sensitive layer, e.g., phosphor, from one side of the plate, e.g., "back side", and reading it off the opposite aspect of the sensitive layer, e.g., "front side". Only one instance of this mode may occur per image. This mode of reflection shall henceforth be referred to as "pre-exposure" reflection in this application. The second mode involves the use of an image processing software tool which reflects right-for-left any selected image. The number of instances of this mode of reflection is not theoretically limited. This mode of reflection shall henceforth be referred to as "software" or "post-exposure" reflection in this application.

Rotation has two distinct modes. The first mode is a physical rotation of the plate, together with its markers, relative to the object to be imaged prior to exposure involved in changing the orientation from "landscape" to "portrait", and if continued, back to "landscape". This mode of rotation shall be referred to henceforth in this application as the "pre-exposure" mode of rotation. The second mode of rotation can occur several ways. After exposure, the PSPs, being small, unattached objects are free to be moved and become randomized in orientation. These PSPs are later removed from their sleeves and arbitrarily rotated as to fit into a plate holder mechanism of the scanner, the constraint at this stage being that the "front side" must face the sensor. Once the images are produced on the computer screen, the operator uses the image processor to align the images in proper superior-inferior orientation by rotating them. This software-mediated rotation is limited to multiples of ninety degrees and is the mechanism through which correct "landscape" and "portrait" orientation as well as superior-inferior relationship is achieved as needed. All three of the rotations given above maintain the relationship between the location of the marker and the details of the shadow-gram. They also preserve laterality. The several mechanisms of rotation comprising the second mode of rotation occur after the sensitive layer is exposed and will henceforth in this application be referred to as "post-exposure" mode of rotation. When a "post-exposure" rotation results in a 180 degree rotation, the resulting transformation is equivalent to a reflection of the entire recorded image through a point located at the intersection of the long and the short axes of symmetry of the plate.

Although certain software-mediated manipulations, such as reflection through a line, are sometimes excluded by built-in restrictions within the radiographic software package, other radiographic software is not so limited. Conventionally, general-usage imaging software does allow such operations and also might be used with an image. Therefore, reflection through a line must be considered possible for any image. This type of "software" or "post-exposure" reflection is discussed below, also.

In order to better understand the discussion below in the DETAILED DESCRIPTION of how the structures according to aspects of the invention unambiguously identify correct and incorrect image orientation, first a discussion of possible transpositions of the image is given.

Within the context of this application, the two modes of reflection and two modes of rotation comprise the universe of orientation transformations allowed by the laws of physics and by the graphic functions included in the software of the image processors typically provided with digital radiography systems. For the purposes of this example, and in order to demonstrate the inability of only a conventional front side marker to differentiate various transformations, a marker 3811, as defined earlier, shall be placed in the lower right corner, as viewed from the "front side", of a plate in a "landscape" orientation. In FIG. 38 the images 3801, 3802, 3803, 3804, 3805, 3806, 3807 and 3808 within the same row (e.g., 3801, 3802, 3803 and 3804; or 3805, 3806, 3807 and 3808) are related to their neighboring images by one ninety-degree "post-exposure" rotation for each step. On the other hand images within the same column (e.g., 3801 and 3805, etc.) are related by a "software", or "post exposure", reflection through a vertical line. As the images 3801, 3802, 3803 and 3804 and also the images 3805, 3806, 3807 and 3808 illustrate, rotation alone allows only two marker 3811 locations each for both the "portrait" and the "landscape" orientations of the image. That is to say that if the image is only rotated (i.e. they lie within the same row in FIG. 38), there are two allowed locations of the marker 3811 for the "landscape" orientation 3801 and 3803 or, the lower right and the upper left corner, and two allowed locations for the marker in the "portrait" orientation 3802 and 3804: lower left and upper right corner of the image. It is also evident from FIG. 38 that for both the "portrait" and for the "landscape" orientation a combination of rotation within the plane and reflection through a line manipulation, as described earlier, is sufficient to generate all the possible locations of the marker. It is also evident that all paths involving an odd number of reflections (i.e. one which generates a net shift of the image to a different row in FIG. 38) are qualitatively different from the paths involving an even number of reflections (i.e., no net shift of row generated in the process). Therefore, assuming an original position of the marker 3811 in the lower right corner in a "landscape" orientation as in image 3801, it is clear that relative to original image 3801, the laterality of image 3803 has not been reversed but that of image 3807 has been. Furthermore, without the knowledge of the original image 3809, 3810 it is possible to deduce its laterality by observation of the marker location and the "portrait" vs. "landscape" orientation of the plate. It should also be noted that teeth of the lower and the upper jaw are significantly enough different to allow their recognition in radiographic images thereby preserving orientation in the superior-inferior dimension. Likewise, anatomical structures elsewhere in the body do not possess another axis of bilateral symmetry than right-left, and can be readily oriented in the anterior-posterior or the superior-inferior dimensions. By analogy, if the long arrow 3810 is assumed to serve as a recognizable index for the superior direction, and the short arrow 3809, the forward direction, then only images 3801 and 3805 represent images properly oriented with respect to the superior-inferior dimension. Furthermore, of those two, only image 3801 has preserved the original laterality of the object casting the shadow. Further complicating the situation is that the plate could have been exposed from the "back side" and viewed from the "front side", resulting in image 3805. This image must be reflected horizontally to be viewed in the "correct" orientation of image 3801.

Suppose, for the purpose of analyzing the images in FIGS. 2, 3, 4 and 5, that the radiology technician, physician, dentist or other exposing this patient's phosphor plate 104 has oriented the "front side" defined above, carrying the open circle, and consequently the sensitive side of the plate 104, toward the X-ray source located at the position SOURCE L, and in the lower right corner of the plate 104 as viewed from the direction of the X-ray source located at the position SOURCE L. FIG. 3 is the image read from the "front side" of the plate 104, when the plate so oriented is exposed by an X-ray source at the location designated SOURCE R. If the viewer reading such an image is aware that the exposure has been made from the "wrong" side, i.e., the "back side", of the plate, the viewer can use image processing software to reorient the image by horizontally flipping the image, as shown in FIG. 2. Mark 201 is transposed from the right to the left, side of the image. The same plate 104, oriented the same way, but exposed from an X-ray source at the location designated SOURCE L, when read from the sensitive side of the plate 104, produces the image shown in FIG. 5. The image of FIG. 4 can be inadvertently produced by manipulation of the image processing software to horizontally flip the image of FIG. 4. Since FIGS. 2 and 4, and FIGS. 3 and 5, are respectively indistinguishable without knowing from which side the plate 104 was exposed, there is no way to determine which side of the patient's jaw the condition 103, seen only in the images in FIGS. 2 and 3, is on. If condition 103 does not produce any externally observable symptoms, the X-ray image may be the only evidence upon which the clinician can rely for determining the location to treat. An ambiguity is introduced into the record that cannot be resolved without another exposure of the patient to radiation. Digital plate technology in its current form does not assure that the orientation of the image can be ascertained. Current technology instead relies on the statistical likelihood that the radiology technician will expose the film correctly vast majority of the time. However, no unambiguous marker of the exposure orientation exists within the image. Moreover, correctly exposed and mounted images do not include a clear, unambiguous mark indicative of that combination of facts, nor do incorrectly exposed and/or mounted images include a clear, unambiguous mark indicative of that combination of facts. Thus, mistakes or malicious mis-orientations are not likely to be recognized. The following four examples illustrate the problem of a lack of an internal reference:

1. If only one image is available for viewing independently of other patient information, the viewer will not be able to identify the correct orientation of the image, except by making an assumption that it was exposed from the "front side".
2. If a radiology technician is consistently making the error of exposing the films from the "back side", unknown to the viewer, the viewer will conclude when comparing images that images (in fact) exposed and oriented correctly are incorrectly oriented (which is not factually correct), thus compounding the problem.
3. A disgruntled or incompetent employee can wreak havoc with the records without anyone realizing it, or having a way of tracing the problem by using software to alter the apparent orientation of images in the records.
4. A person with fraudulent intent can expose the plate intentionally from the "back side" in order to make the image appear as though it depicts the opposite side of the body.

The analysis of FIGS. 6, 7, 8 and 9 is similar to FIGS. 2, 3, 4 and 5, respectively, except for the initial orientation of the plate. These images are produced by a plate 104 oriented with an open circle, and consequently the sensitive side of the plate 104 oriented toward the X-ray source located at the position SOURCE L, but in the top left corner of the plate as viewed from the direction of the X-ray source located at the position SOURCE L.

FIGS. 10, 11, 12 and 13 represent images produced by a plate 104 oriented with an open circle, and consequently the sensitive side of the plate 104 oriented toward the X-ray source located at the position SOURCE R, but in the bottom right corner of the plate as viewed from the direction of the X-ray source located at the position SOURCE R.

FIG. 10 shows the image produced by SOURCE R, in which the open circle 201 is in the lower right corner. FIG. 11 can be inadvertently produced by a horizontal flip of the image of FIG. 10 using image processing software. FIG. 12 shows the result of exposing the plate using SOURCE L. In order to view the image in an orientation expected by the clinician, the image of FIG. 12 can be horizontally flipped to produce the image of FIG. 13. Similarly to the situation described above in connection with FIGS. 2, 3, 4 and 5, FIGS. 10 and 12 are inherently indistinguishable, as are FIGS. 11 and 13.

The analysis of FIGS. 14, 15, 16 and 17 is similar to FIGS. 10, 11, 12 and 13, respectively, except for the initial orientation of the plate. These images are produced by a plate 104 oriented with the open circle, and consequently the sensitive side of the plate 104 oriented toward the X-ray source located at the position SOURCE R, but in the top left corner of the plate as viewed from the direction of the X-ray source located at the position SOURCE R.

Direct Radiography or Digital Radiography

An alternate technology which is competing with PSPs to replace conventional film employs electronic sensors. These sensors may use CCD, CMOS, thin-film transistor (TFT), or the like, construction design and are similar to those used in digital cameras and camcorders. The image is recorded by capturing a shadow cast by the radiation which has been attenuated by passage through tissues under examination and then falling onto the sensor. The sensors are constructed in the shape of a parallelepiped with rounded corners for patient comfort and with two opposing roughly rectangular sides that correspond in size and shape to standard dental film. The thickness of the sensor is several millimeters. During use the sensors are typically connected to a computer or other data acquisition device through a direct cable or a wireless data transmission system. Because of the required electronic circuitry and other radiopaque elements, known sensors have only surface capable of recording an image.

Some of the manufacturers incorporate into their sensors features that produce marks within the image. These marks vary in shape but might be a small rectangle in a corner (Schick, Dexis) or the letters "RVG" along one of the edges in a corner (Trophy/Practiceworks/Kodak). After the image is processed and displayed, the marks, when present, appear as part of the image and behave in exactly the same ways as those marks produced by the front side marker in conventional PSPs. That is to say, manipulations such as rotations and reflections of the image change the location and orientation of the mark in precisely the same way as they would if it were a detail of the diagnostic image itself.

These characteristics of sensor-based radiography eliminate one source of orientation error from consideration, namely the pre-exposure mode or reflection of the image. This means that one can conclude unambiguously whether or not the image has been reversed through reflection if one knows which corner of the sensor has the marker. However, the portrait vs. landscape and rotations related to superior-inferior orientation of the image in the mount can still be disorienting and produce confusion regarding the laterality of the image. Such rotations might particularly affect the wireless sensors which do not require a wire fed out between the lips and to the acquisition device. The wired systems generally obey the following rules because of their direct connection and the stiffness of the wire:

1. the wire is anterior for posterior "landscape"-oriented sensor placement
2. the wire is superior for mandibular anterior "portrait"-oriented sensor placement
3. the wire is inferior for maxillary anterior "portrait"-oriented sensor placement Any other placement, e.g., vertical bitewing, need not follow any particular rule as a matter of wire placement convenience.

As a consequence of the above factors, the orientation issues presented by the sensor-based systems are varied. For example, laterality identification problems vary from absolute lack of orientation clues in images produced by systems without built-in markers, particularly in those situations where wire lead location is noncontributory (e.g., vertical bitewings) to less serious in other configurations. Those with an asymmetrically placed symmetric marker can be traced if one knows the location on the sensor of the marker which yielded the mark in the image, but without that knowledge laterality can be absolutely ambiguous. If the location of the marker producing the mark is absolutely known to lie in the, for sake of argument, lower right corner when in "landscape" orientation of the sensor, then the clues to laterality can be reduced to the following rules:

1. If the mark is in the lower right or the upper left in a "landscape" orientation of the image, the image laterality is correct,
2. If the mark is in the upper right or the lower left in a "portrait" orientation of the image, the image laterality is correct,
3. If the combination of the mark location and image orientation is different in any aspect then the image is reversed, Similar rules apply, but with the "sensors" being opposite, as may be understood by the skilled artisan, if the marker were known to be in the upper left in "portrait" orientation of the sensor. The tracing of the marks and their indication of the laterality requires knowledge of details which are not naturally obvious, concentration, attention, an innate ability to manipulate objects in space, and time. In a clinical setting these might not be available when needed.

The marker which produces "RVG" logo mark in the corner of the image is significantly easier to use as an orientation clue to laterality because of the chirality of the mark produced by the "RVG" marker. Flipping of an image containing the mark will also flip the mark. When the letters are visible in their natural orientation, this reflection is easily recognized by an observer. However when the letters within the mark are either upside down or the mark is oriented vertically rather than horizontally, the reflected mark is not nearly as clearly recognizable as being reflected; therefore its value as a tool for detecting reversed laterality of the image is diminished.

SUMMARY OF INVENTION

A radiation-recording plate can be constructed and arranged to form an image upon exposure from both a front side and a back side. The plate can include a marker detectable in the image after exposure and indicative of which of the front side and the back side the plate is exposed from. The marker may comprise a medium opaque to the radiation coating a region that does not interfere with reading the image when the plate is exposed from either side. The plate may be sensitive to X-radiation, and the medium may comprise one or more of a heavy element, an alloy including a heavy element, a compound including a heavy element or a salt of a heavy element. The medium could be one of Pb, Sn, Bi, I, Cu and Ba. The medium could be a heavy metal suspended in a binder applied to the region. The marker may have asymmetry about at least one axis. The marker may have horizontal asymmetry about a vertical axis relative to a normal image orientation, or the marker may have vertical asymmetry about a horizontal axis relative to a normal image orientation. The marker may further comprise a back side marker whose appearance in an image on the plate indicates exposure from the back side.

The plate may have a layer sensitive to the radiation that is readable only from the front side, the back side marker further comprising at least one of a material that enhances reading of the sensitive layer and a material that attenuates reading of the sensitive layer. Such a back side marker may further comprise at least one of a material that enhances exposure of the plate in a defined region and a material that attenuates exposure of the plate in the defined region. The back side marker may further comprise one of a heavy element, an alloy including a heavy element, a compound including a heavy element or a salt of a heavy element. The medium may be one of Pb, Sn, Bi, I, Cu and Ba.

The plate may further comprise a front side marker whose appearance in an image on the plate indicates exposure from the front side. This plate may further have a layer sensitive to the radiation that is readable at least from the front side, the front side marker further comprising at least one of a void defined in the layer sensitive to the radiation, a material that enhances a signal returned in the area of the marker when reading the sensitive layer and a material that attenuates the signal returned in the area of the marker when reading the sensitive layer or a material having some property different from the rest of the layer sensitive to the radiation such as the frequency of the stimulated emission light. The plate may be readable only from the front side by exciting the layer sensitive to the radiation with an excitation wavelength to generate a return signal at a return signal wavelength, the front side marker functionally opaque to at least one of the excitation signal wavelength and the return signal wavelength. The front side marker may further comprise one of a heavy element, an alloy including a heavy element, a compound including a heavy element or a salt of a heavy element. The medium may be one of Pb, Sn, Bi, I, Cu and Ba. The front side marker may further comprise a void defined in the layer sensitive to the radiation.

The marker may have asymmetry about at least one axis and the marker further comprising a front side marker and a back side marker. The marker can have either horizontal asymmetry about a vertical axis or vertical asymmetry about a horizontal axis, relative to a normal image orientation. In this case, the front side marker may further comprise: a region defined to have a shape of an arrow pointed in a first direction when viewed from the front side. The back side marker may further comprise: a region defined to have a shape of an arrow pointed in a second direction different from the first direction when viewed from the front side. The back side marker, whether arrow-shaped or otherwise having a cognizable left-right and/or top-bottom orientation, can be positioned so as to obscure the front side marker when the plate is exposed from the back side and read from the front side. The plate may include another sensitive layer, wherein the back side marker is disposed between the sensitive layer and the other sensitive layer, and the plate further comprising another front side marker relative to the other sensitive layer.

A method of identifying a side from which a radiation-recording plate has been exposed to radiation may comprise: incorporating in the plate, in a position that substantially does not interfere with an image area of the plate, a marker that produces a mark whose appearance in the image identifies which side the plate is exposed from; exposing the plate to the radiation; and observing the image for the identification of the side of the plate exposed. The mark so produced may be observable and understandable to humans or by machines and may be embedded in such a way as to be undetectable without machine assistance. The method may further comprise: arranging the marker to indicate a rotational orientation of the plate; and observing the image for the indication of the rotational orientation of the plate. The method may yet further comprise observing the image using image processing software, the image processing software recognizing the mark and reorienting an image of the plate to have a clinically expected orientation. The method may yet further comprise performing other alterations to the image, such as introducing a visible mark. The method may yet further comprise: storing with the image an indication of whether the image has been reoriented by an odd number of times. The method may also comprise: substituting for the mark a replacement mark indicative of the software having processed the image; storing the image with the replacement mark or eliminating the triggering mark. This method may also further comprise: storing with the image an indication of whether the image has been reoriented by an odd number of times. The indication stored may be a humanly visible mark or a machine-readable mark.

Such a third mark, sometimes referred to herein as a replacement mark, software generated mark, or an orientation confirming mark, can be used with either PSP systems or sensor systems of image capture. In the PSP environment it can be inserted into the image after the presence or absence of a back side marker is detected and the orientation of the image is determined during processing. The presence of this mark, which at least in part might be inserted into the diagnostic image by the processing software, and the recognition of its correct orientation by the viewer, will allow the viewer of the image to confirm that the orientation of the viewed image containing it has not been reversed through either pre-exposure or post-exposure modes of reflection. This would hold true for images that have been rendered as hard copy on paper or film (viewable from either side) or rendered as an image on an electronic monitor by software capable of reflection operation.

In the PSP systems which use both the reflection on detection algorithm and the back side marker as described herein and which apply these capabilities to all plate processing, the front side marker need not be required on the plate itself for unambiguous maintenance of orientation information. The software generated mark in the image obviates the need for the front side mark since it provides more complete and easier to use orientation information than that deduced from the presence of the mark produced by the front side marker and prevents the need for potentially spurious graphics from the image. Furthermore, the processing software, by design, will insert the confirmation mark into the image before the image is rendered for viewing. However the presence of the front side mark might be desirable for other reasons, such as confirmation in the image of the brand of PSP used.

In sensor based systems which use software capabilities described in this application the orientation confirmation mark provides for unambiguous orientation of a diagnostic image without the need for any additional information about the nature of the sensor or any markers associated with it. An alternate method of producing an orientation confirming mark in the image is through constructing the sensor in such manner that multiple recognizably asymmetric marks which possess a recognizable conventional orientation are produced in the latent image or the image file stored by the equipment to which the sensor is connected, prior to software processing. This might include blinding the sensor cells by blocking radiation from reaching them, rendering them incapable of recording the incident radiation, depriving them of connection to the data acquisition device, or otherwise.

Consequently the recognition of the described orientation confirmation mark in the diagnostic image is sufficient to allow for proper orientation of an isolated image with reference to reflection manipulations. For all intraoral, and most other, dental images that is equivalent to identifying the laterality. For medical images in which the direction of the incident ray (e.g., anterior-posterior vs. posterior-anterior) can be identified from the image itself, the anatomical orientation is also confirmed through the use of this method. In systems using plate-holding cassettes such as certain large-format medical PSP systems which ensure that the plate is exposed from only one side, the orientation confirmation mark would immediately indicate the condition of reversed laterality to the viewer of such an image by appearing in the image in reversed orientation.

Desirable characteristics of an orientation-confirmation mark include:

1. The mark may possess elements of rotational symmetry but should lack bilateral symmetry. Such a combination of symmetry/asymmetry might render the appearance of the mark in the image indistinguishable to the reader of the image regardless of any of the standard rotational positions that the image might be mounted in, but because of its lack of bilateral symmetry in at least the horizontal axis and the vertical axis, reflections of its image would be readily evident to the reader.
2. The mark may incorporate symbols such as letters, digits, and other graphics which generally possess a recognizable, expected orientation. Elements of the mark may further be recognizable as words or text.
3. The inclusion of these characters singly, in groupings, overlapping, or separated, and in orientations to one another which do or do not place the recognizable shapes in coincident parallel axes of orientation might constitute the construction of such a mark.
4. The mark can be an aggregation of graphics introduced by software with graphics already present in the image as a result of another image processing operation such as the front side mark produced by a marker on a PSP or a mark produced by a built in marker on a sensor. The orientation confirming mark might be a composite of graphics introduced into the diagnostic image during several distinct stages of registering and processing of the radiographic shadowgram including the initial capture of incident radiation.
5. The mark can be incorporated into the image once the laterality of the image is determined by program algorithms which might include such considerations as the source of the data (e.g., sensor or plate), the presence or lack of possibility of pre-exposure mode of image reflection, the presence or absence of back side marker shadow, the flipping or reflection of the image if it is deemed to be reversed relative to its expected orientation and appearance, the recognition of own-brand capture device and its characteristics, and others.
6. The mark can be inserted into an area of the image which is not of diagnostic value.
7. The mark can be opaque or alternatively can change the values of the pixel values of underlying image while preserving an aspect of their relative intensity.
8. The mark in a sensor-produced image can consist entirely of elements produced by markers built into the sensor structure which possess the features described herein.

A method of making a radiation sensitive plate having at least one radiation sensitive layer may comprise: providing a film sensitive to the radiation on a first side of the radiation sensitive plate; and applying a suspension of a heavy metal in a binder to a region of a second side of the radiation sensitive layer.

A method for preserving orientation information in an image may comprise: collecting image data, including orientation information inherent to collecting the image data; and embedding in the image data an orientation mark unambiguously identifying when the image data is presented in a correct viewing orientation. Variations of the method are possible, including wherein collecting includes forming in the image data an exposure mark indicative of from which side of an image receptor radiation incident upon a target object was then incident upon the image receptor. The method may further include: detecting the exposure mark; interpreting the exposure mark; and determining a correspondence between the correct viewing orientation of the image data and the interpreting of the exposure mark; and wherein embedding further comprises: orienting the orientation mark according to the determined correspondence. The method may yet further be varied, wherein embedding further comprises rendering the orientation mark substantially inseparable from the image data. In yet a further variation, the method further comprises: including with the image data and embedded orientation mark, validation data from which a determination can be made that the embedded orientation mark and the image data are validly associated and are unaltered after embedding the orientation mark.

According to yet other embodiments of aspects of the invention, image data is stored in a medium together with data forming an embedded orientation mark which is bilaterally asymmetrical in at least two orthogonal axes. In a variation, the data forming the embedded orientation mark further comprises at least one humanly recognizable text or punctuation character. In yet a further variation, the data forming the embedded orientation mark further comprises at least one humanly recognizable word. Another variation has the data forming the embedded orientation mark further comprising at least one humanly recognizable trademark.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 6 is a representation of an image produced by exposing a conventional digital dental X-ray plate having a "front side" facing left through the right side of the patient's mandible, scanning the image from the "front side" of the plate, and flipping the image horizontally;

FIG. 7 is a representation of an image produced by exposing a conventional digital dental X-ray plate having a "front side" facing left through the right side of the patient's mandible and scanning the image from the "front side" of the plate;

FIG. 8 is a representation of an image produced by exposing a conventional digital dental X-ray plate having a "front side" facing left through the left side of the patient's mandible, scanning the image from the "front side" of the plate, and flipping the image horizontally;

FIG. 9 is a representation of an image produced by exposing a conventional digital dental X-ray plate having a "front side" facing left through the left side of the patient's mandible and scanning the image from the "front side" of the plate;

FIG. 10 is a representation of an image produced by exposing a conventional digital dental X-ray plate having a "front side" facing right through the right side of the patient's mandible and scanning the image from the "front side" of the plate;

FIG. 11 is a representation of an image produced by exposing a conventional digital dental X-ray plate having a "front side" facing right through the right side of the patient's mandible, scanning the image from the "front side" of the plate, and flipping the image horizontally;

FIG. 12 is a representation of an image produced by exposing a conventional digital dental X-ray plate having a "front side" facing right through the left side of the patient's mandible and scanning the image from the "front side" of the plate;

FIG. 13 is a representation of an image produced by exposing a conventional digital dental X-ray plate having a "front side" facing right through the left side of the patient's mandible, scanning the image from the "front side" of the plate, and flipping the image horizontally;

FIG. 14 is a representation of an image produced by exposing a conventional digital dental X-ray plate having a "front side" facing right through the right side of the patient's mandible and scanning the image from the "front side" of the plate;

FIG. 15 is a representation of an image produced by exposing a conventional digital dental X-ray plate having a "front side" facing right through the right side of the patient's mandible, scanning the image from the "front side" of the plate, and flipping the image horizontally;

FIG. 16 is a representation of an image produced by exposing a conventional digital dental X-ray plate having a "front side" facing right through the left side of the patient's mandible and scanning the image from the "front side" of the plate;

FIG. 17 is a representation of an image produced by exposing a conventional digital dental X-ray plate having a "front side" facing right through the left side of the patient's mandible, scanning the image from the "front side" of the plate, and flipping the image horizontally;

FIG. 18 is a representation of an image produced by exposing a digital dental X-ray plate having a "front side" facing left and embodying aspects of the invention through the right side of the patient's mandible, scanning the image from the "front side" of the plate, and flipping the image horizontally;

FIG. 19 is a representation of an image produced by exposing a digital dental X-ray plate having a "front side" facing left and embodying aspects of the invention through the right side of the patient's mandible and scanning the image from the "front side" of the plate;

FIG. 20 is a representation of an image produced by exposing a digital dental X-ray plate having a "front side" facing left and embodying aspects of the invention through the left side of the patient's mandible, scanning the image from the "front side" of the plate, and flipping the image horizontally;

FIG. 21 is a representation of an image produced by exposing a digital dental X-ray plate having a "front side" facing left and embodying aspects of the invention through the left side of the patient's mandible and scanning the image from the "front side" of the plate;

FIG. 22 is a representation of an image produced by exposing a digital dental X-ray plate having a "front side" facing left and embodying aspects of the invention through the right side of the patient's mandible, scanning the image from the "front side" of the plate, and flipping the image horizontally;

FIG. 23 is a representation of an image produced by exposing a digital dental X-ray plate having a "front side" facing left and embodying aspects of the invention through the right side of the patient's mandible and scanning the image from the "front side" of the plate;

FIG. 24 is a representation of an image produced by exposing a digital dental X-ray plate having a "front side" facing left and embodying aspects of the invention through the left side of the patient's mandible, scanning the image from the "front side" of the plate, and flipping the image horizontally;

FIG. 25 is a representation of an image produced by exposing a digital dental X-ray plate having a "front side" facing left and embodying aspects of the invention through the left side of the patient's mandible and scanning the image from the "front side" of the plate;

FIG. 26 is a representation of an image produced by exposing a digital dental X-ray plate having a "front side" facing right and embodying aspects of the invention through the right side of the patient's mandible and scanning the image from the "front side" of the plate;

FIG. 27 is a representation of an image produced by exposing a digital dental X-ray plate having a "front side" facing right and embodying aspects of the invention through the right side of the patient's mandible, scanning the image from the "front side" of the plate, and flipping the image horizontally;

FIG. 28 is a representation of an image produced by exposing a digital dental X-ray plate having a "front side" facing right and embodying aspects of the invention through the left side of the patient's mandible and scanning the image from the "front side" of the plate;

FIG. 29 is a representation of an image produced by exposing a digital dental X-ray plate having a "front side" facing right and embodying aspects of the invention through the left side of the patient's mandible, scanning the image from the "front side" of the plate, and flipping the image horizontally;

FIG. 30 is a representation of an image produced by exposing a digital dental X-ray plate having a "front side" facing right and embodying aspects of the invention through the right side of the patient's mandible and scanning the image from the "front side" of the plate;

FIG. 31 is a representation of an image produced by exposing a digital dental X-ray plate having a "front side" facing right and embodying aspects of the invention through the right side of the patient's mandible, scanning the image from the "front side" of the plate, and flipping the image horizontally;

FIG. 32 is a representation of an image produced by exposing a digital dental X-ray plate having a "front side" facing right and embodying aspects of the invention through the left side of the patient's mandible and scanning the image from the "front side" of the plate;

FIG. 33 is a representation of an image produced by exposing a digital dental X-ray plate having a "front side" facing right and embodying aspects of the invention through the left side of the patient's mandible, scanning the image from the "front side" of the plate, and flipping the image horizontally;

FIG. 54 is an image of a mark in "correct" orientation produced by a marker according to aspects of an embodiment of the invention;

FIG. 55 is an image of a mark in "correct" orientation produced by a marker according to aspects of an embodiment of the invention, which has been rotated 90 degrees;

FIGS. 56 and 57 are images of a mark in "mirrored" orientation produced by a marker according to aspects of an embodiment of the invention, which are also rotated by various amounts;

DETAILED DESCRIPTION

Figure 1:
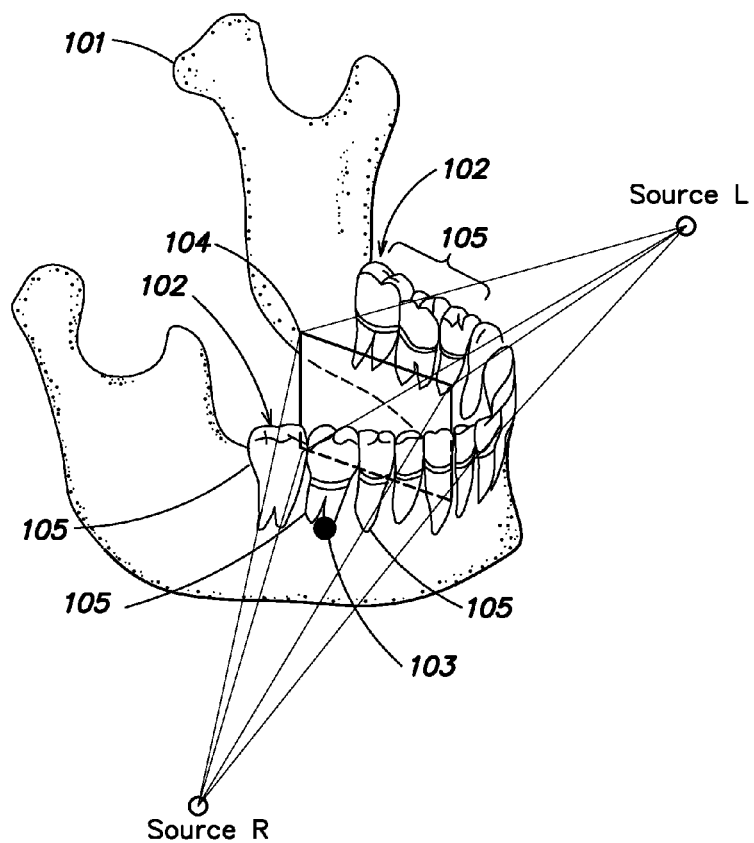
FIG. 1 is a perspective view of a human mandible and teeth showing how a dental X-ray plate is exposed from both the left and right sides.
Figure 2:
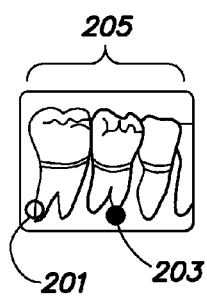
FIG. 2 is a representation of an image produced by exposing a conventional digital dental X-ray plate having a "front side" facing left through the right side of the patient's mandible, scanning the image from the "front side" of the plate, and flipping the image horizontally using software.
Figure 3:
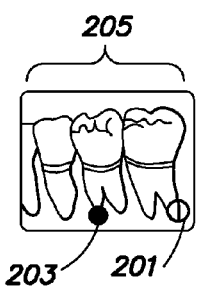
FIG. 3 is a representation of an image produced by exposing a conventional digital dental X-ray plate having a "front side" facing left through the right side of the patient's mandible and scanning the image from the "front side" of the plate.
Figure 4:
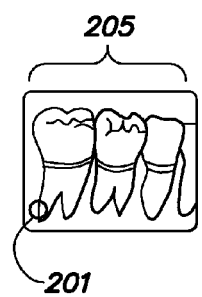
FIG. 4 is a representation of an image produced by exposing a conventional digital dental X-ray plate having a "front side" facing left through the left side of the patient's mandible, scanning the image from the "front side" of the plate, and flipping the image horizontally using software.
Figure 5:
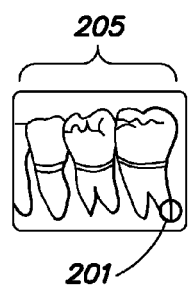
FIG. 5 is a representation of an image produced by exposing a conventional digital dental X-ray plate having a "front side" facing left through the left side of the patient's mandible and scanning the image from the "front side" of the plate.

A detailed description of various aspects of embodiments of the invention follows. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

According to aspects of embodiments of the invention, exposure of one side of a radiosensitive plate produces one indicator pattern in the image, while exposure of the other side of the radiosensitive plate produces a different indicator pattern in the image. The indicator pattern recorded on the radiosensitive plate becomes a permanent part of a data pattern recorded by the particular exposure. Thus, whether the data set is embodied in the radiosensitive plate, a digital image data file, or a displayed or printed image, the indicator pattern forms a permanent part of the record. The indicator pattern may blanket the image or may be localized. It may render an image exposed through a substrate of the plate unusable, or may only minimally degrade image quality, or may be located so as not to degrade the quality of the image or data set in any way, for example by being small and located outside of a primary image forming area, such as in a corner of a rectangular plate.

Because the means for forming the indicator pattern is a permanent part of the plate, put there at the time of manufacture, no single or repetitive operator act is required to mark plates with their direction of exposure, no protocol to ensure exposure from a particular side of a plate is required, unless an indicator of a type rendering the image unusable when exposed from a "wrong side" is used, and the indication of the direction of exposure is unambiguously embedded in any data set produced from such a plate. No special protocol or specification of protective sleeves is required for image orientation purposes, either, unless an indicator of a type rendering the image unusable when exposed from a "wrong side" is used.

The indicator pattern can further be used to help identify laterality, i.e., "handedness," of an image. Preservation of the laterality of an image may be important because the symmetry inherent in the human body and most higher animal forms makes distinguishing between certain structures, such as a patient's left incisor or hip and the patient's right incisor or hip, difficult independently, i.e. without other sources of identification. In the case of intraoral dental radiographs, laterality is fully defined by the direction of exposure and the structure depicted. This is so because the radiation source for intraoral dental X-rays is always located outside the patient's mouth and the sensitized plate is always located within the patient's mouth.

Several different structures that produce indicator patterns having the characteristics discussed above and which unambiguously identify each of the possible transpositions are now described in detail. There are two independent non-overlapping categories of markers, "front side" markers and "back side" markers.

A "front side" marker is one that produces a mark in an image viewed or scanned from the front side, regardless of the side of exposure, while a "back side" marker is one that produces a mark in an image on a plate exposed from the "back side" and subsequently read from the "front side". In general, the marker patterns can be produced by materials having suitable patterns placed intermediate the plate sensitive layer and the source of exposing radiation. These patterns can alternatively be produced on phosphor storage plates by affecting the excitation and recording the resultant phosphorescence of the phosphor during the scan process, for example, by perforating the phosphor layer, by obscuring it, or by otherwise altering the phosphorescence properties of the phosphor layer, such as using a phosphor with different excitation properties or different phosphorescence properties (e.g., different wavelength of stimulating or emitted energy) For example, materials can, using any suitable process, be coated, printed, painted, laminated, sublimated, bonded, riveted, etc. onto the plate surfaces during the fabrication process. The materials can be selected to partially or wholly block or intensify, e.g. by use of different phosphor, the radiation reaching the plate in the area covered. A common material that blocks X-radiation, and can be usefully applied to the plates in laminated form in paints or in inks, is lead. Other heavy metals or other heavy elements can also be used, in various forms, e.g., foils, grains, etc. of copper, lead, tin, bismuth, barium, etc. Here, heavy metals and heavy elements generally include any element from the fourth row of the periodic table and heavier. One particularly useful material is copper foil having an approximate thickness of about 1 mil or thicker. Such foil is available in adhesive-backed forms which can be laser cut or die cut to desired form and applied to plates during manufacture.

One example of the type of plate to which the principles of the invention are applicable is a dental plate including a plastic substrate onto which is coated a storage phosphor material sensitive to dental X-rays. The plates are produced in large sheets or continuous webs and then die-cut into their final size and shape.

A simple embodiment is now described, in which a plate such as just described, readable from one side, i.e., the "front side", has an indicator pattern-forming material, i.e., a marker, incorporated into such plate on the opposite side of the plane of the sensitive layer from which such plate is read. This is a "back side" marker.

In this embodiment, a mark is printed on the "back side", in one corner thereof. The mark is printed using a lead impregnated paint, or other suitable material. Other suitable constructions are described in greater detail, below. When exposed from the "front side" of the plate, the resulting image includes no mark. However, when exposed from the "back side" of the plate, an unexposed mark is formed in that portion of the image corresponding to the corner of the plate on which the mark is printed. The image produced, including the mark, can take the form of any of the images of FIGS. 2-33. The mark need not have any special shape because the information desired can be simply derived from the presence or absence in the image of the mark. Images produced by exposing the plate from one side or the other are distinguishable in the same manner as described below in connection with FIGS. 18, 19, 20 and 21, for example. According to this embodiment, only a "back side" marker is required in contrast to conventional media which use only a "front side" marker.

In a second embodiment, both a "front side" marker and a "back side" marker may be present. For example, different patterns of indicator-forming material may be applied to opposite sides of a plate readable from one side. Alternatively, the "front side" marker may be one or more perforations in the phosphor. This embodiment is advantageous in that the indicator pattern formed can unambiguously inform a person reading the resulting image from which direction the plate was exposed, whereas when the plate of the first embodiment is exposed from the direction that produces no indicator pattern, the image is indistinguishable from images produced by PSPs not including any markers or flipped horizontally.

Embodiments of the invention incorporating both a "front side" marker and a "back side" marker can fully indicate the orientation of a structure imaged, even when the position of the radiation source and the radiation sensitive plate relative to the structure is unknown.

If the plate is marked by both a "front side" marker and a "back side" marker, as described in connection with the second embodiment, the direction of exposure of the plate is unambiguously recorded in the image without any intervention or special act by the operator. In addition, the cassette or sleeve in which the plate is placed during exposure can include a radiopaque mark on one or both sides, unambiguously indicating the proper orientation of the cassette or sleeve relative to some absolute reference such as the left side or front of the patient.

FIGS. 18, 19, 20 and 21 illustrate four images that can be produced using a PSP according to this embodiment of aspects of the invention, exposed from each of two sides, using each of two differently located sources, e.g., positioned at SOURCE L and SOURCE R. This embodiment has an open circle mark on the X-ray sensitive side of the plate, in one corner, and a filled circle mark on the other side of the plate, in this case in the same corner. In using this embodiment, attention need not be paid to which side faces the source because, as explained below, different marks appear on the image produced, depending on the side from which the plate is exposed.

Suppose, for the purpose of analyzing the images in FIGS. 18, 19, 20 and 21, that the radiology technician, physician, dentist or other exposing this patient's PSP 104 has oriented the open circle, and consequently the sensitive side of the plate 104, toward the X-ray source located at the position SOURCE L, and in the lower right corner of the plate 104 as viewed from the direction of the X-ray source located at the position SOURCE L. In this embodiment, the filled circle is on the opposite side of the plate 104, in the same corner as the open circle. FIG. 19 is the image read from the sensitive side of the plate 104, when the plate so oriented is exposed by an X-ray source at the location designated SOURCE R. The clinician reading such an image will recognize that it was exposed from the reverse side of the plate 104 because of the presence of the closed circle 1801 and use image processing software to reorient the image by horizontally flipping the image so the filled circle 1801 appears in the expected corner of the image, as shown in FIG. 18. Note that it is known that the filled mark, as described above, is oriented to the bottom-left corner of the plate 104, and must appear in that corner when the image is properly oriented, i.e., oriented so that structures are depicted in their natural and expected orientation. Thus, it is clear that FIG. 18 represents the correct orientation of the image exposed through the back of the plate 104. The same plate 104, oriented the same way, but exposed from an X-ray source at the location designated SOURCE L, when read from the sensitive side of the plate 104, produces the image shown in FIG. 21. The image of FIG. 20 can be inadvertently produced by manipulation of the image processing software to horizontally flip the image of FIG. 21. However, it is known that FIG. 21 must be the correct orientation because the open mark is located, as described above, in the lower-right corner of the plate 104. Since FIGS. 18 and 21 are clearly and unambiguously the correctly oriented images, the radiology technician, physician, dentist or other person reading the images knows with certainty that the condition 203 is on the patient's right side.

Like FIGS. 18, 19, 20 and 21, FIGS. 22, 23, 24 and 25 illustrate four images that can be produced using a PSP according to this embodiment of aspects of the invention, exposed from each of two sides, using each of two differently located sources, e.g., positioned at SOURCE L and SOURCE R. This embodiment has an open circle mark on the X-ray sensitive side of the plate, in one corner, and a filled circle mark on the other side of the plate, in this case in the same corner. In the embodiment illustrated by the resulting images in FIGS. 22, 23, 24 and 25, the marks are located in a top corner, rather than a bottom corner, as explained below. In using this embodiment, attention need not be paid to which side faces the source because, as explained below, different marks appear on the image produced, depending on the side from which the plate is exposed.

Suppose, for the purpose of analyzing the images in FIGS. 22, 23, 24 and 25, that the radiology technician, physician, dentist or other exposing this patient's digital dental X-ray plate 104 has oriented the open circle, and consequently the sensitive side of the plate 104, toward the X-ray source located at the position SOURCE L, and in the upper left corner of the plate 104 as viewed from the direction of the X-ray source located at the position SOURCE L. In this embodiment, the filled circle is on the opposite side of the plate 104, in the same corner as the open circle. FIG. 23 is the image read from the sensitive side of the plate 104, when the plate so oriented is exposed by an X-ray source at the location designated SOURCE R. The clinician reading such an image will recognize that it was exposed from the reverse side of the plate 104 because of the presence of the closed circle 1801 and use image processing software to reorient the image by horizontally flipping the image so the filled circle 1801 appears in the expected corner of the image, as shown in FIG. 22. Note that it is known that the filled mark, as described above, is oriented to the top-right corner of the plate 104, and must appear in that corner when the image is properly oriented. Thus, it is clear that FIG. 22 represents the correct orientation of the image exposed through the back of the plate 104. The same plate 104, oriented the same way, but exposed from an X-ray source at the location designated SOURCE L, when read from the sensitive side of the plate 104, produces the image shown in FIG. 25. The image of FIG. 24 can be inadvertently produced by manipulation of the image processing software to horizontally flip the image of FIG. 25. However, it is known that FIG. 25 must be the correct orientation because the open mark is located, as described above, in the top-left corner of the plate 104. Since FIGS. 22 and 23 are clearly and unambiguously the correctly oriented images, the radiology technician, physician, dentist or other person reading the images knows with certainty that the condition 103 is on the patient's right side.

FIGS. 26, 27, 28 and 29 illustrate four images that can be produced using a PSP according to this embodiment of aspects of the invention, exposed from each of two sides, using each of two differently located sources, e.g., positioned at SOURCE L and SOURCE R. This embodiment has an open circle mark on the X-ray sensitive side of the plate, in one corner, and a filled circle mark on the other side of the plate, in this case in the same corner. In using this embodiment, attention need not be paid to which side faces the source because, as explained below, different marks appear on the image produced, depending on the side from which the plate is exposed.

Suppose, for the purpose of analyzing the images in FIGS. 26, 27, 28 and 29, that the radiology technician, physician, dentist or other exposing this patient's digital dental X-ray plate 104 has oriented the open circle, and consequently the sensitive side of the plate 104, toward the X-ray source located at the position SOURCE R, and in the lower right corner of the plate 104 as viewed from the direction of the X-ray source located at the position SOURCE R. In this embodiment, the filled circle is on the opposite side of the plate 104, in the same corner as the open circle. FIG. 26 is the image read from the sensitive side of the plate 104, when the plate so oriented is exposed by an X-ray source at the location designated SOURCE R. The clinician reading such an image will recognize that it was exposed from the sensitive side of the plate 104 because of the presence of the open circle 201. However, the image could be inadvertently or intentionally reoriented by horizontally flipping the image so the open circle 201 appears in the lower left corner of the image, as shown in FIG. 27. Note that it is known that the open mark, as described above, is oriented to the bottom-right corner of the plate 104, and must appear in that corner when the image is properly oriented, i.e., oriented so that structures are depicted in their natural and expected orientation. Thus, it is clear that FIG. 26 represents the correct orientation of the image exposed through the sensitive side of the plate 104. The same plate 104, oriented the same way, but exposed from an X-ray source at the location designated SOURCE L, when read from the sensitive side of the plate 104, produces the image shown in FIG. 28. The image of FIG. 29 can be produced by manipulation of the image processing software to horizontally flip the image of FIG. 28, so as to locate the closed circle 1801 in the lower left corner of the image, as expected for an image produced by exposing the plate 104 from the "back side" of the plate. It is known that FIG. 29 must be the correct orientation because the closed mark is located, as described above, in the lower-left corner of the plate 104. Since FIGS. 26 and 29 are clearly and unambiguously the correctly oriented images, the radiology technician, physician, dentist or other person reading the images knows with certainty that the condition 103 is on the patient's right side.

Like FIGS. 26, 27, 28 and 29, FIGS. 30, 31, 32 and 33 illustrate four images that can be produced using a PSP according to this embodiment of aspects of the invention, exposed from each of two sides, using each of two differently located sources, e.g., positioned at SOURCE L and SOURCE R. This embodiment has an open circle mark on the X-ray sensitive side of the plate, in one corner, and a filled circle mark on the other side of the plate, in this case in the same corner. In the embodiment illustrated by the resulting images in FIGS. 30, 31, 32 and 33, the marks are located in a top corner, rather than a bottom corner, as explained below. In using this embodiment, attention need not be paid to which side faces the source because, as explained below, different marks appear on the image produced, depending on the side from which the plate is exposed.

Suppose, for the purpose of analyzing the images in FIGS. 30, 31, 32 and 33, that the radiology technician, physician, dentist or other exposing this patient's digital dental X-ray plate 104 has oriented the open circle, and consequently the sensitive side of the plate 104, toward the X-ray source located at the position SOURCE R, and in the upper left corner of the plate 104 as viewed from the direction of the X-ray source located at the position SOURCE R. In this embodiment, the filled circle is on the opposite side of the plate 104, in the same corner as the open circle. FIG. 30 is the image read from the sensitive side of the plate 104, when the plate so oriented is exposed by an X-ray source at the location designated SOURCE R. The clinician reading such an image will recognize that it was exposed from the sensitive side of the plate 104 because of the presence of the open circle 201. However, the image could be inadvertently or intentionally reoriented by horizontally flipping the image so the open circle 201 appears in the upper right corner of the image, as shown in FIG. 31. Note that it is known that the open mark, as described above, is oriented to the upper-left corner of the plate 104, and must appear in that corner when the image is properly oriented. Thus, it is clear that FIG. 30 represents the correct orientation of the image exposed through the sensitive side of the plate 104. The same plate 104, oriented the same way, but exposed from an X-ray source at the location designated SOURCE L, when read from the sensitive side of the plate 104, produces the image shown in FIG. 32. The image of FIG. 33 can be produced by manipulation of the image processing software to horizontally flip the image of FIG. 32, so as to locate the closed circle 1801 in the upper right corner of the image, as expected for an image produced by exposing the plate 104 from the "back side" of the plate. It is known that FIG. 33 must be the correct orientation because the closed mark is located, as described above, in the lower-left corner of the plate 104. Since FIGS. 30 and 33 are clearly and unambiguously the correctly oriented images, the radiology technician, physician, dentist or other person reading the images knows with certainty that the condition 103 is on the patient's right side.

Figure 39:
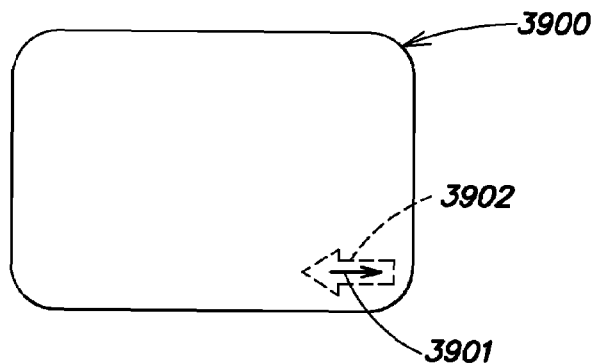
FIG. 39 is a plan view of a plate showing the relative positions of a "front side" marker (solid) and a "back side" marker (phantom)

In a third embodiment of the invention, shown in FIG. 39, the markers are asymmetric, are asymmetrically placed with respect to the plate surface axes of symmetry, and both "front side" and "back side" markers are employed. In the example, the markers 3901 and 3902 are made in the shape of arrows. Of course, markers 3901 and 3902 could be any suitable directional marker meeting the further requirements described in connection with this embodiment. Let us further suppose that the "front side" marker 3901 is a thin, short, horizontally directed arrow pointing at the right vertical edge of the plate at the lower edge of image 3900, while the "back side" marker 3902 is a solid arrow, also horizontally directed at the lower edge of a "landscape" oriented plate, but pointing away from the vertical edge of the plate of image 3900. For purpose of illustration, by virtue of their size and placement on the opposite sides of plane defined by the plate, the relationship between the markers 3901, 3902 produces an overlap between the image of the two markers. In this particular arrangement, when the plate is exposed from the "back side" and then scanned, the two arrows overlap producing an image of the larger solid arrow of the "back side" marker on the plate image and obscuring the thinner "front side" marker. Thus, only one arrow shows in any exposed and scanned plate image.

Figure 38:
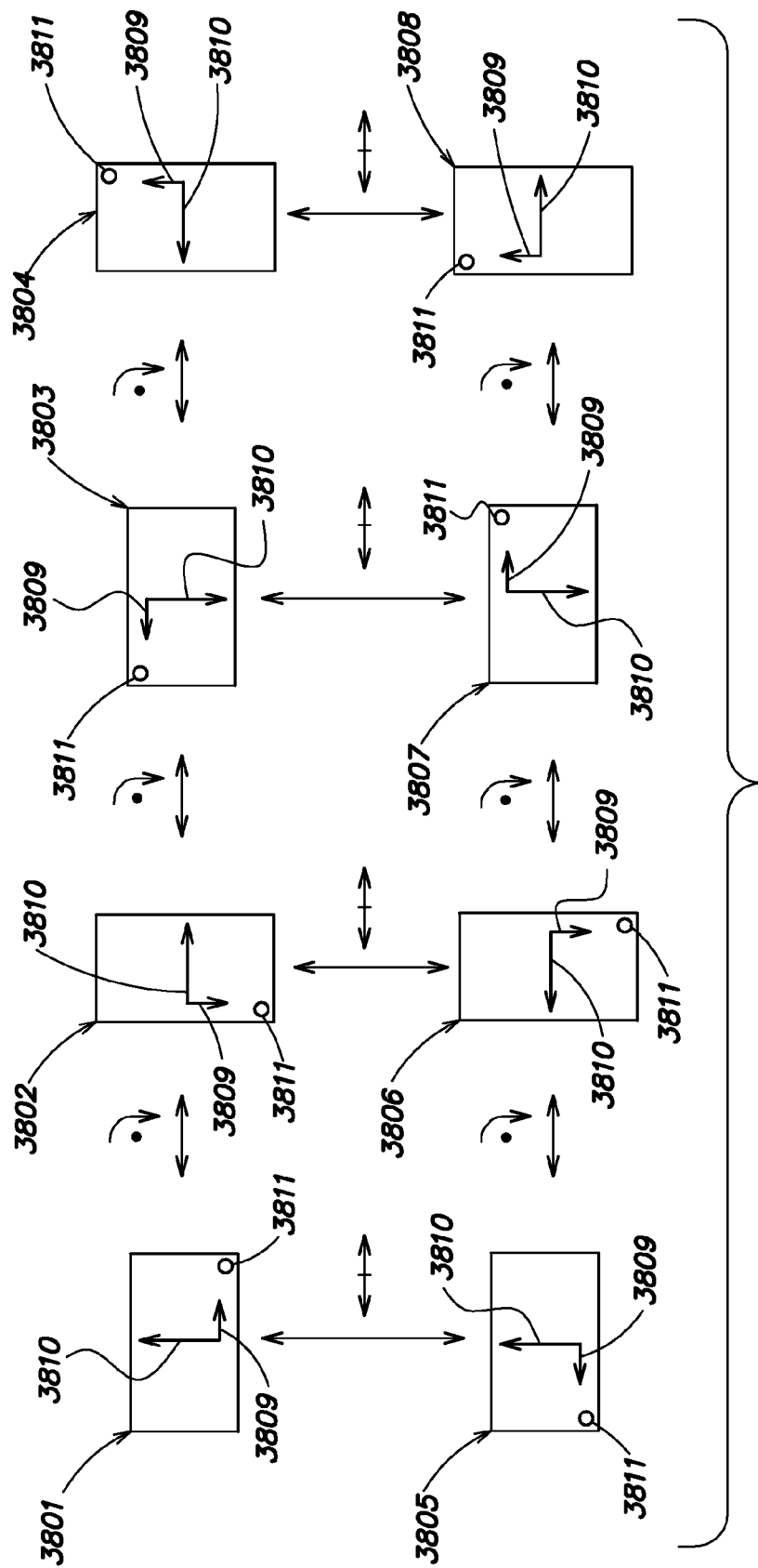
FIG. 38 is a transposition map illustrating the relationships between various transpositions of an image.

In extending the method of analysis used in the discussion relating to FIG. 38 to this third embodiment of the invention, all possible landscape images that can be produced with exposure from the "front side" and then manipulated through the plane rotations and reflections described earlier are illustrated in FIG. 40. In the interest of simplicity of the illustration only "landscape" orientation of the image need be discussed presently: By virtue of the relative ease in finding the superior-inferior orientation, it is for practical reasons nearly impossible to confuse two, intraoral dental images, as well as images of many other anatomical structures, which are related to each other by a rotation of ninety degrees because a horizontal image and a vertical image have teeth aligned either with the short or the long axis of the plate, an easily discriminated condition. Furthermore, the different orientations of the plate are typically used in different applications. "Portrait" orientation is generally used with anterior tooth periapical and also vertical bitewing studies, whereas "landscape" orientation is used with posterior tooth periapical and also horizontal bitewing studies. Also, it has been already demonstrated earlier in the discussion regarding FIG. 38 relative to "landscape" oriented images, that this method of analysis can be extended to and is valid for "portrait" oriented images.

Figure 40:
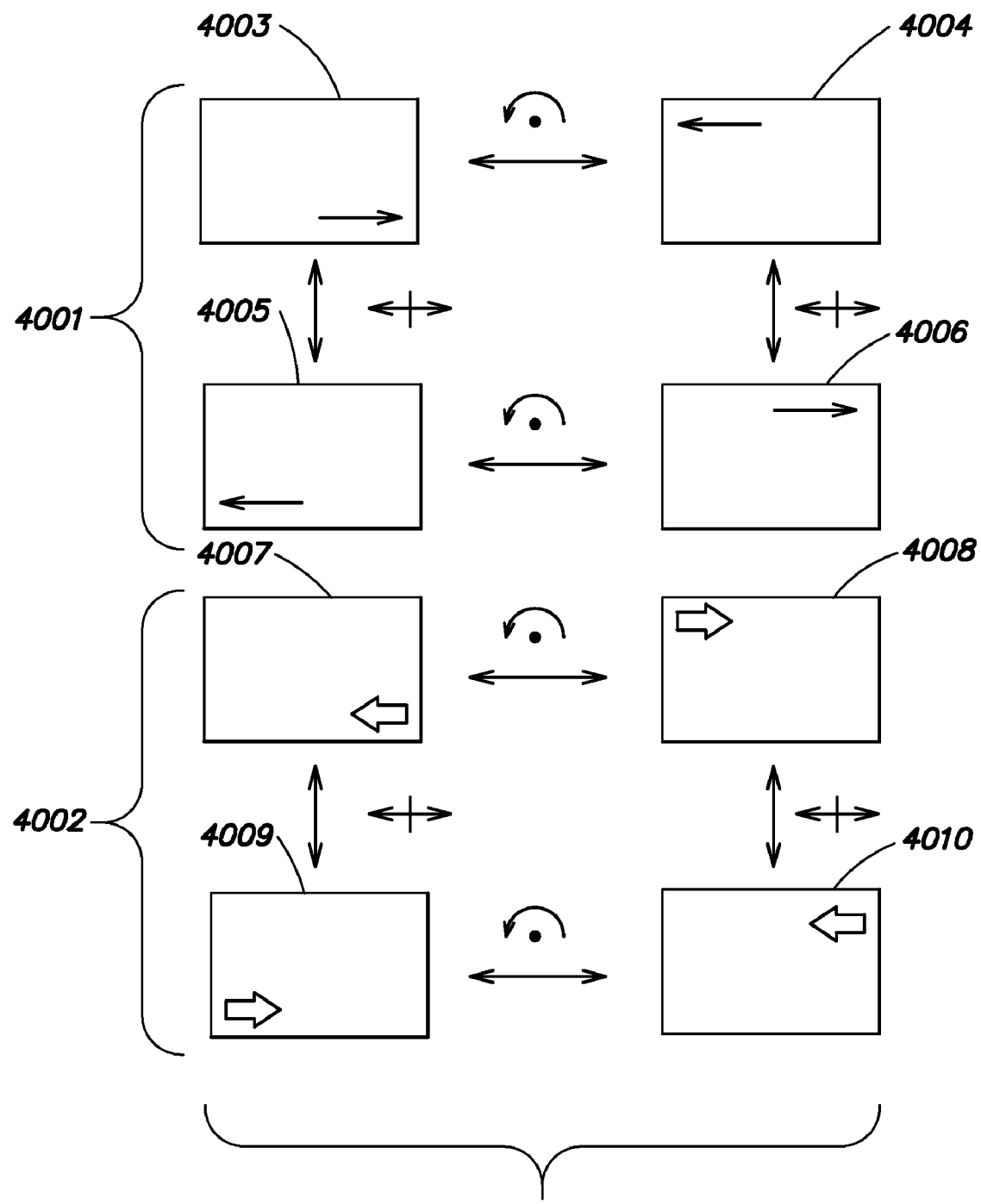
FIG. 40 is a transform map of the plate of FIG. 39.
Figure 42:
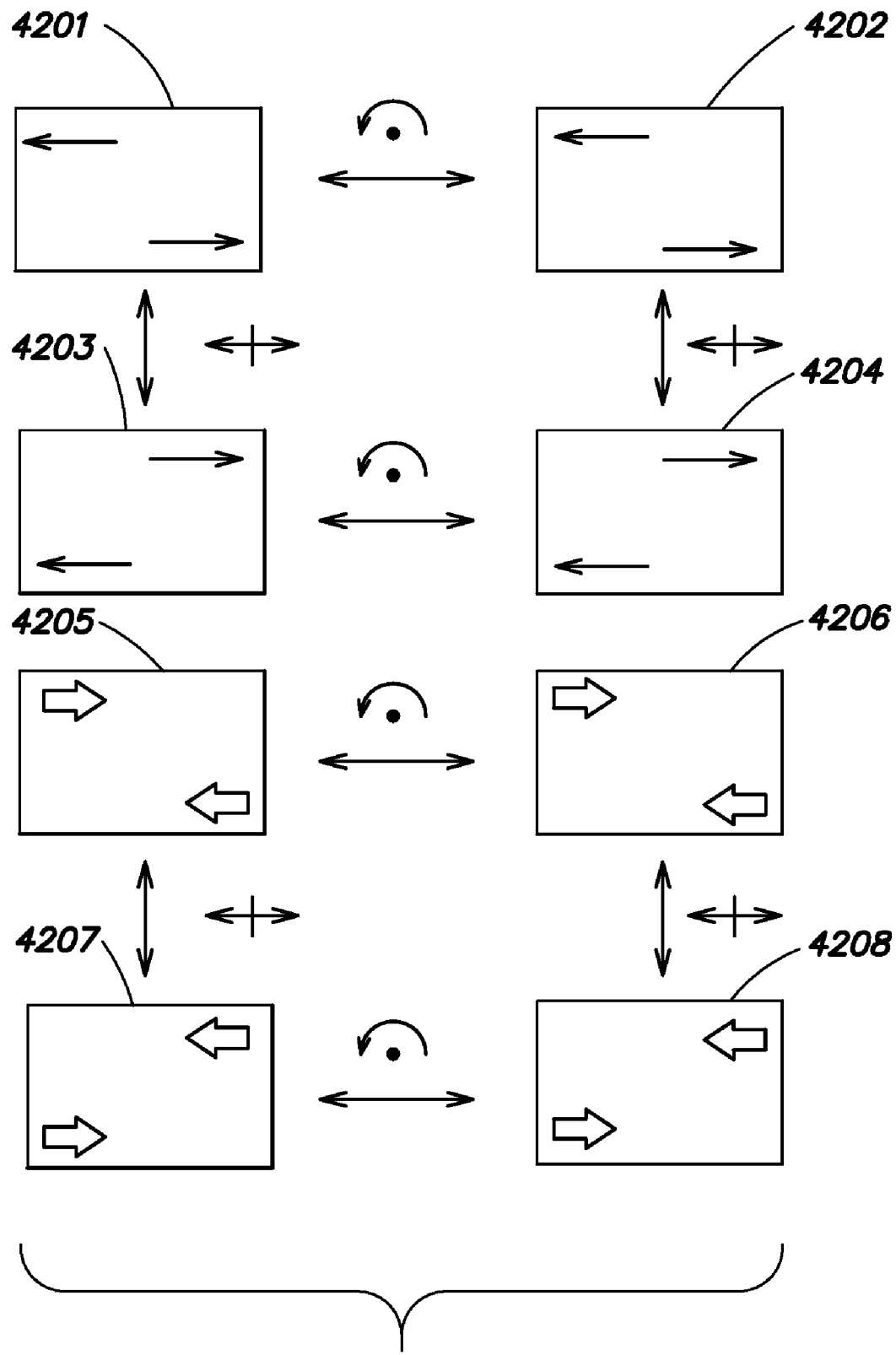
FIG. 42 is a transform map of the plate of FIG. 41.

The following discussion of FIG. 40 extends the method of analysis applied regarding FIG. 38 to the third embodiment of the invention. The two motions, a 180 degree rotation around an axis perpendicular to the plane of the plate (or the image) at the intersection of its long and short axis, and a reflection through a vertical plane perpendicular to the plane of the image, are the four modes of manipulation which, singly or when combined, produce all allowed orientations of the image.

The first mode is "pre-exposure" reflection of the plate, changing whether the plate is exposed from the "front side" or from the "back side". Depending on which initial reflection position a plate has been exposed in, one of group 4001 and 4002 will be the starting point of analysis.

The second mode of manipulation is a physical rotation of the plate prior to exposure involved in changing the orientation from "portrait" to "landscape", and if continued, back to "landscape", and which changes the relationship between the location of the marker and details of the image produced by the shadow-gram. As has been demonstrated in the discussion regarding FIG. 38 and FIGS. 2 through 33 there exists equivalence between the two possible orientations attainable through this mode within the "landscape" orientation, and by extension also within the "portrait" orientation; therefore, further discussion of this manipulation will be deferred after stating that this rotation mode produces an effect on an asymmetric, or asymmetrically placed, marker which is equivalent to a reflection through a point located at the intersection of the plate's long and short axis of symmetry. Which initial exposure rotation has occurred determining whether the starting point for analysis of an image will be in the left column of images or the right column of images in FIG. 40.

The third mode, a rotation of the plate after exposure, when mounted into the scanner or by software once the data has been captured, maintains the relationship between the location of the marker and the details of the shadow-gram. As discussed below, this mode is illustrated by movements between the left and right columns of FIG. 40. This mode is referred to as "post-exposure" rotation.

The fourth mode is software reflection of the image after capture. This manipulation is illustrated in FIG. 40 by vertical movement between rows, while remaining within the original group 4001 or 4002.

A plate having "front side" markers and "back side" markers, exposed from an arbitrary side and then manipulated by image processing software will produce one of the images of FIG. 40, as noted above. Analysis of those images is discussed below in connection with four hypothetical starting points 4003, 4004, 4007 and 4008.

Hypothetical #1

An image scanned from a plate exposed in the conventionally "correct" orientation, that is, with the "front side" marker facing the source of radiation and at the lower edge is shown in image 4003. Software manipulations by rotation or reflection can produce any of images 4004, 4005, or 4006 in group 4001. However, note that the thin, "front side" marker arrow is at the lower edge facing right when the image 4003 is correctly oriented.

Hypothetical #2

An image as scanned from a plate exposed from the "front side", but rotated so that the "front side" marker is at the upper edge producing the scanned image 4004. Again, software manipulation can produce any of the images 4003, 4005 and 4006. When correctly oriented for viewing, this image 4004 has the thin, "front side" marker arrow at the upper edge facing left.

Hypothetical #3

According to this hypothetical, the plate is exposed from the "back side", with the "back side" marker in the lower edge. When scanned, image 4007, with the "back side" marker on the lower right, facing left is produced. Because this image was subject to a pre-exposure reflection, the scanned image 4007 is produced. A software reflection produces the correct image 4009. Although images 4008 and 4010 could also be produced by software manipulation, observe that "correct" image 4009 has the thick, "back side" marker arrow at the lower edge facing right.

Hypothetical #4

According to this last hypothetical, the plate is exposed from the "back side" after being rotated so that the "back side" marker is at the upper edge, producing scanned image 4008. In order to view the image in a "correct" orientation, it is manipulated using software to reflect horizontally the image 4008, to produce image 4010. The corrected image 4010 has the thick, "back side" marker arrow at the upper edge facing left.

A simple rule can be derived from the four foregoing hypothetical using aspects of the third embodiment, whereby any image produced using the embodiment can be quickly and accurately oriented correctly for viewing. For landscape mode images, after orienting an image correctly with respect to superior/inferior parts using rotation, any marker arrow at the top edge of the image should point left, any marker arrow at the bottom edge of the image should point right. The image must, using software, be reflected horizontally to achieve correct orientation if the rule is not met initially.

Figure 41:
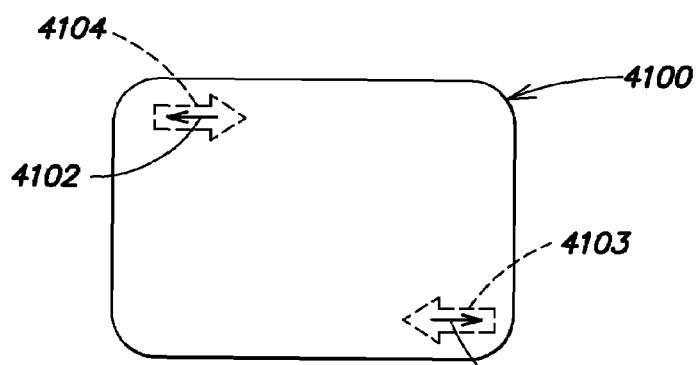
FIG. 41 is a plan view of a plate showing the relative positions of dual "front side" markers (solid) and dual "back side" markers (phantom)

In a fourth embodiment of the invention, illustrated in FIG. 41, two "front side" 4101, 4102 and two "back side" markers 4103, 4104 are used in the following manner. The relationship between markers 4101, 4103 and 4104 is similar to that described in connection with markers 3901 and 3902 of the third embodiment. However, a second set of markers 4102, 4104 bearing a similar relationship is located at the point of reflection of the first set through a line passing perpendicularly through the center of the face of the plate.

All the possible images 4201-4208 generated by scanning such a plate exposed to a radiation source from the "front side" and from the "back side" are shown in corresponding positions to those of FIG. 40. The arrows associated with the properly oriented images all point to the right if they are in the lower half of the image and to the left if they are in the upper half of the image, making the rule stated above even easier to apply. Such design of the marker shape and location in the processed image facilitates not only accurate and unambiguous orientation but also further reduces the number of decisions that an operator must make in the process of arranging the images in the mount, thus reducing the time required for the operation.

Furthermore, even if one of the markers should be obscured by the shadow of a clinical structure which is radiopaque, e.g., a metallic filling or crown, the other is present to even in this rare situation provide indication of the laterality of the image.

In a yet another embodiment of the invention, the plate is fitted with two layers of sensitive material, each possessing a small "front side" marker and allowing the mechanism which converts the latent image into a visible diagnostic image to read the plate from either or both sides and producing a recognizable pattern of that marker in such a diagnostic image, and a different indicator-forming marker or material, housed between the two sensitive layers, capable of producing a recognizable pattern, preferably obscuring the image of the "front side" marker as in the foregoing embodiment, readable from either of the sensitive layers if such material lies between a radiation source and that layer.

Figure 44A:
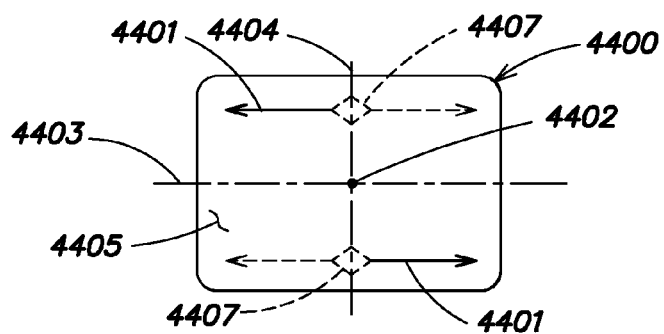
FIGS. 44A & 44B is a plan views of a double-phosphor plate showing the relative positions of a "front side" marker (solid arrow, phantom arrow) and a "back side" marker (phantom diamond) when viewed from either side, and representing exposure and viewing from the same side.
Figure 44B:
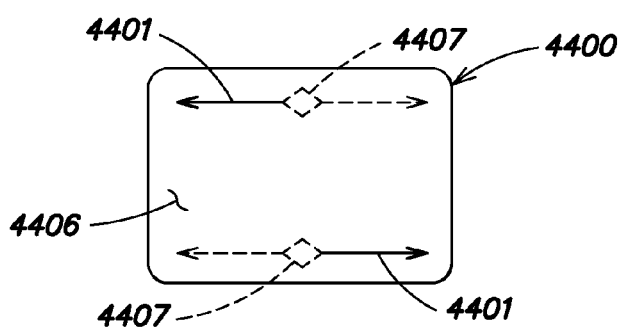

An example of aspects of this embodiment is shown by the plate 4400 illustrated in FIGS. 44A and 44B. The "front side" marker set FIG. 44A is comprised of two pairs, one pair on each side, of two arrows 4401, arranged on the plate in the following manner: each arrow, lying along and near a long edge of the plate, originates near the midpoint of the nearest long edge and points toward the right short edge if it is located near the lower long edge, or toward the left short edge if lying near the upper long edge. The same arrangement of arrows is present on the reverse side of the plate. The two arrows reflect onto one another through the point of intersection 4402 of the long 4403 and the short 4404 axes of symmetry of the plate as represented in FIGS. 44A and 44B. The resulting "front side" marker configuration is such that the two sides 4405 and 4406 of the plate are indistinguishable from one another, both having phosphor coating and arrows which lie in identical positions relative to one another through any manipulations that preserve the "landscape" or "portrait" orientation of the plate 4400, i.e. any 180 degree or multiple thereof, rotation about any of the principal axes 4403 and 4404 of symmetry or the point 4402 of symmetry.

Figure 45:
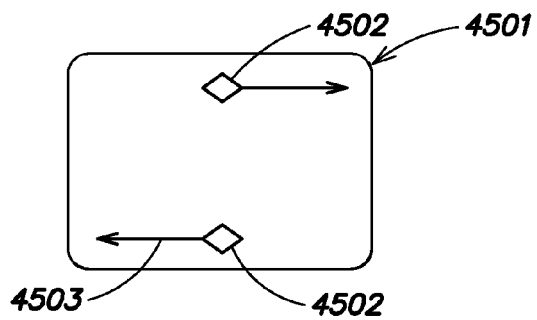
FIG. 45 is a plan view of an image produced by a double-phosphor plate showing the relative positions of the "front side" marker and the "back side" marker when exposed from one side and viewed from the other side, after the image has been flipped horizontally.

According to further aspects of this embodiment, between the two phosphor film layers lie near the tail ends of each of the four arrows 4401, radiopaque medium deposits 4407 which can cast a shadow onto the phosphor on the side of the plate opposite the source of radiation and the radiographed object. In the landscape orientation (as shown), the above arrangement of arrow-shaped "front side" markers 4401 and internal material 4407 comprising a "back side" marker, any image of an object exposed from and read from the same side of the plate will have proper orientation, as always, as scanned, with the lower edge arrow 4401 pointing to the right and the "back side" marker 4407 shadow absent. On the other hand, as shown in FIG. 45, any image 4501 of an object exposed from one side of the plate and read from the other will reveal the "back side" marker image 4502, which will appear at the right side, i.e. the tail, of the lower arrow 4503 when the diagnostic image has been properly oriented by the software. An image with the lower arrow (FIG. 44, 4401) pointing right in the absence of the "back side" marker shadow has also been properly oriented. However, an image (not shown) with a "back side" marker shadow present at the left end, i.e. the tail, of the "front side" marker would indicate an image in which right and left are reversed and requiring software reflection for proper orientation of the diagnostic image. As with the previous embodiments similar analysis generates simple rules for proper image orientation.

As seen from the above discussion, PSPs according to the various embodiments described produce images with distinctive markers permanently embedded in the image information. The distinctive markers can be recognized and acted upon by the clinician viewing the images, or can be automatically recognized and acted upon by the image processing software used to view the images. More sophisticated software can first perform the superior/inferior orientation on its own, based on any suitable image processing rules, while less sophisticated software can rely on the operator to first perform the superior/inferior orientation. In order to effect automatic orientation recognition and reorientation, the image processing software would next search the known possible locations of the markers for those particular shapes corresponding to the markers. When one of those shapes is found in one of those possible locations of the markers, a rule for correctly orienting the image is then applied. In the case of the third or fourth embodiments described above, the simple rule set forth above can easily be applied automatically by the software to bring each image immediately into its correct orientation. The software can also be written to replace a marker recognized within an image with one of its own. The substitution would help those using the images recognize that they have been processed and correctly oriented.

Another software enhancement is also possible in connection with aspects of embodiments of the invention. The reflection process performed by the image processing software can modify the file by toggling a "reflection flag" indicative of whether the image has been reflected an odd or even number of times. The reflection flag can be embedded within the image file, can be stored in an independent file, can be part of the image file name, or stored in any other suitable location. The value of the reflection flag can represent one of two states.

The reflection process and reflection flag would preferably satisfy the following conditions:
1. The reflection process flips the reflection flag state from one to the other, each time a reflection was applied to a given image, thereby tracking the number of reflections, modulo two;
2. The image file so processed is modified to include a graphic, text or other indication, that the image has been reflected horizontally (through a vertical axis of reflection); and
3. The repeated use of the reflection tool would toggle the reflection flag between the two states each time it is used.

The image processing system would display a correctly oriented image either if the "back side" marker were present and the reflection flag were indicating an odd number of reflection operations, or if the "back side" marker were absent and the reflection flag indicated an even (including zero) number of reflection operations.

Figure 86:
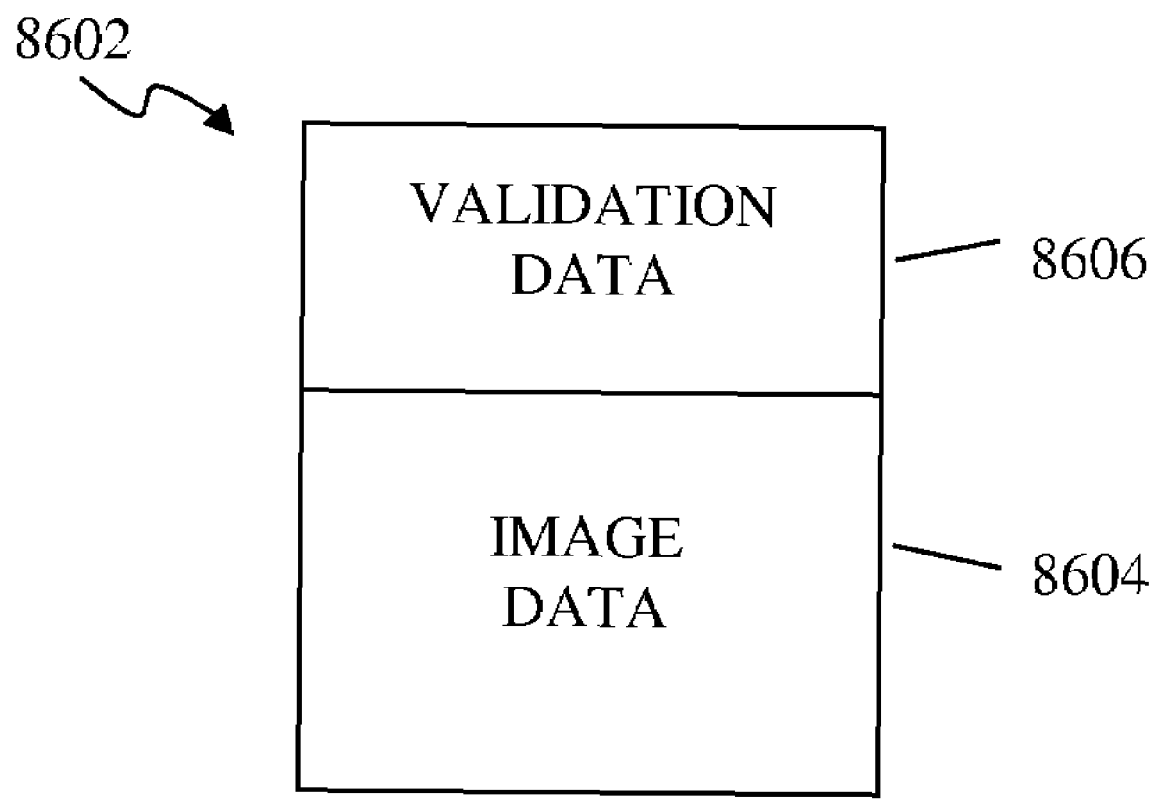
FIG. 86 is a diagram of a stored image file including image data and validation data.

In another embodiment of the invention, the image processing system may store validation data along with the image data, as illustrated schematically in FIG. 86. In FIG. 86, the image processing system stores a data file 8602 which includes an image data portion 8604 and a validation data portion 8606. The validation data 8606 can be used at a later time to verify that no modification of the image data has occurred.

Plates embodying aspects of the invention can be manufactured by any suitable method. The mark to be produced can be of any arbitrary size relative to the size of the PSPs to be produced. In production methods in which one or more PSPs are cut from larger sheets or webs of material coated on one side with phosphor or another radio-sensitive material, placement of the mark can be synchronized with the locations from which the PSPs are cut, may be randomly placed relative to the locations from which the PSPs are cut, or may completely blanket the locations from which the PSPs are cut. Synchronization can be achieved by any suitable method, including those known in the printing arts for aligning printed elements and die cuts.

A small, highly distinctive mark can be placed in a consistent, predetermined location, whereas a blanket pattern used as the mark should also be highly distinctive, so as to distinguish it from patterns likely to be seen in the diagnostic image. Preferable blanket patters are rectilinear or angular, rather than mottled, curved or random, so as to be distinguishable from naturally occurring patterns in the diagnostic image.

As noted above, production of the mark or pattern on the plate can be done using any suitable means of varying the transmission or absorption of the diagnostic radiation.

For example, the substance of the plate which carries the phosphor might be manufactured in such a way that its absorption of the radiation which produces the latent image in the phosphor is not uniform. The non-uniformity can take the form of the desired mark or pattern. Examples of processes capable of producing the desired non-uniformity are now described.

Alternatively, also as noted above, production of the mark or pattern can be done by varying the output of an exposed plate, for example by varying the phosphor type, thickness or presence.

The pattern can be an integral part of the bulk substance of a plate having a non-uniform composition. This can be accomplished by the introduction of a material which would locally increase the extinction coefficient of the radiation and produce a recognizable pattern in the shadow cast on the phosphor when exposed from its side of the phosphor. During manufacture, a radio-opaque material, e.g. heavy metal salt powder of an appropriate particle size, can be added to the material from which the plate is formed. This addition can be performed in such way that the material would not become homogeneous prior to the finishing of the plate for example while the materials are in a semi-flowable state, before hardening into finished sheets.

The pattern can be introduced during the manufacturing of the plate as a modification of the sheet which holds the phosphor of the finished plate. Examples which can be combined as desired, include to hot press, adhere, stamp, print with ink or foil, spray, re-sublimate, dust, inlay, or otherwise deposit, or impress into, the sheet a material of different extinction coefficient than the bulk material of the sheet. This would introduce a recognizable pattern into the shadow cast onto the phosphor when exposed from its side.

Figure 34:
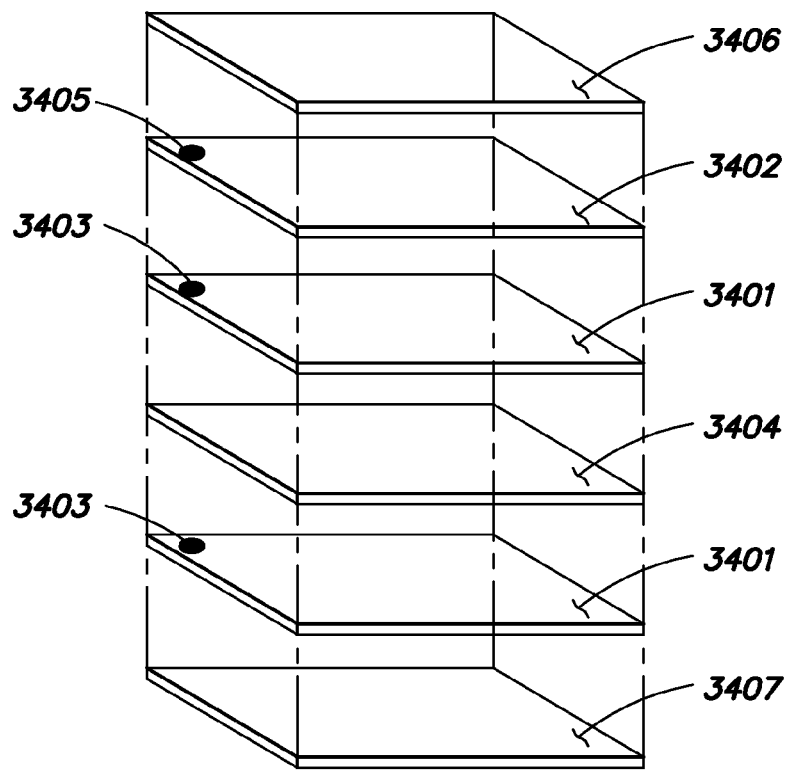
FIG. 34 is an exploded view of a laminate having radiopaque indicator marks according to aspects of the invention.

As shown in FIG. 34, the sheet from which the plate is made may be a laminate or sandwich structure in which at least one layer 3401 is capable of casting a non-uniform shadow onto the phosphor 3402. That layer 3401, for example, might be a metallic foil cutout providing the label pattern 3403. Alternatively, the non-uniform layer might be obtained by one of the other methods, above which is then laminated into a finished structure. The layer 3401 is applied to one side of a substrate 3404, while the phosphor layer 3402, with a material 3405 casting a non-uniform shadow thereon, is applied to the other side of the substrate 3404. Protective layers 3406 and 3407 are applied to the outer surfaces of the structure. One potential advantage of this approach is that a method of deposition which might be inappropriate because of instability, e.g. mechanical or chemical, of the radiopaque deposit might become acceptable by sealing the deposited material inside the sandwich, thereby making it stable between the layers. Another advantage is that an otherwise convenient material which, because of undesirable properties such as toxicity, might be excluded from consideration as a surface coating, might be useable if present only in small amounts, safely sealed within the structure of the plate. Such materials might be powders, inks, or foils containing heavy metals, elements, their alloys, compounds or salts.

Figure 35:
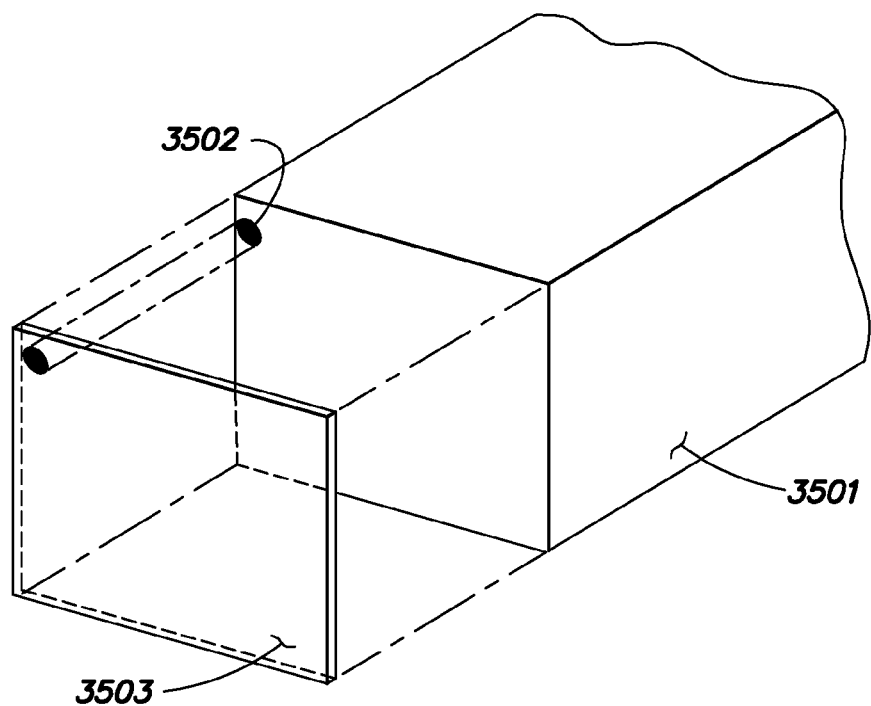
FIG. 35 is a perspective view of a bulk material having an inlaid radiopaque material and a slice cut off of the bulk material, wherein the slice can be used in constructing a PSP according to aspects of the invention.

Another method for producing zones of contrasting radiopacity within the plate is to inlay the substrate of the plate with a full or partial thickness of material possessing a significantly different coefficient of extinction at relevant wavelengths. One way to create a full thickness inlay of this type, as shown in FIG. 35, is by transversely sectioning a non-homogeneous extrusion block 3501, having embedded therein a material 3502 capable of casting a non-uniform shadow onto the phosphor (FIG. 34, 3402, for example), where each transverse section 3503 is thin enough to be used as an individual plate.

Figure 36:
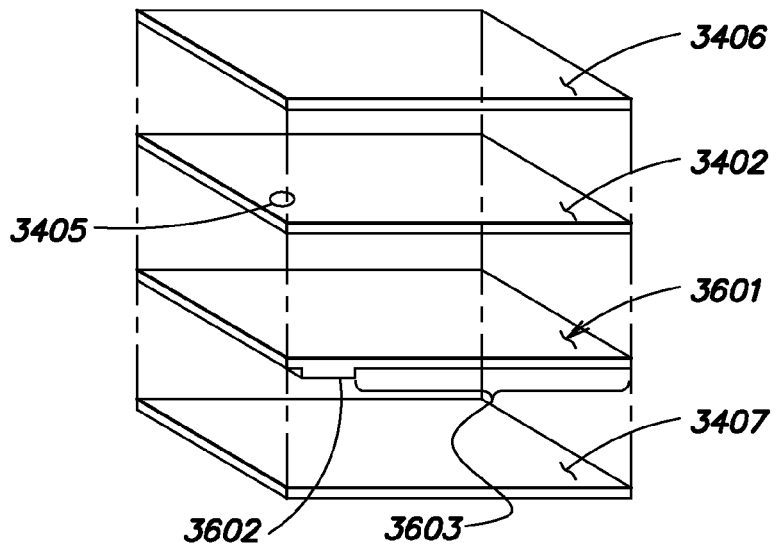
FIG. 36 is an exploded view of a radiographic plate produced using a radiopaque substrate whose thickness is varied to produce a unique marker when exposed through the substrate.

According to another structure, shown in FIG. 36, the plate is made of a material which itself has a substantial degree of radiopacity, the variation in the intensity of the shadow cast by the plate when exposed from one side might also be produced by varying the thickness of the substrate 3601 onto which the phosphor is deposited. The substance of which the plate is made would, in this example, need to possess a significant extinction coefficient for the wavelength of radiation used in the exposure. For a substrate including, for example, a heavy metal, a thick region 3602 would cast a more intense shadow than a thinner region 3603. To protect a patient from heavy metal exposure and to improve durability, protective layers 3406 and 3407 are also included.

Figure 37:
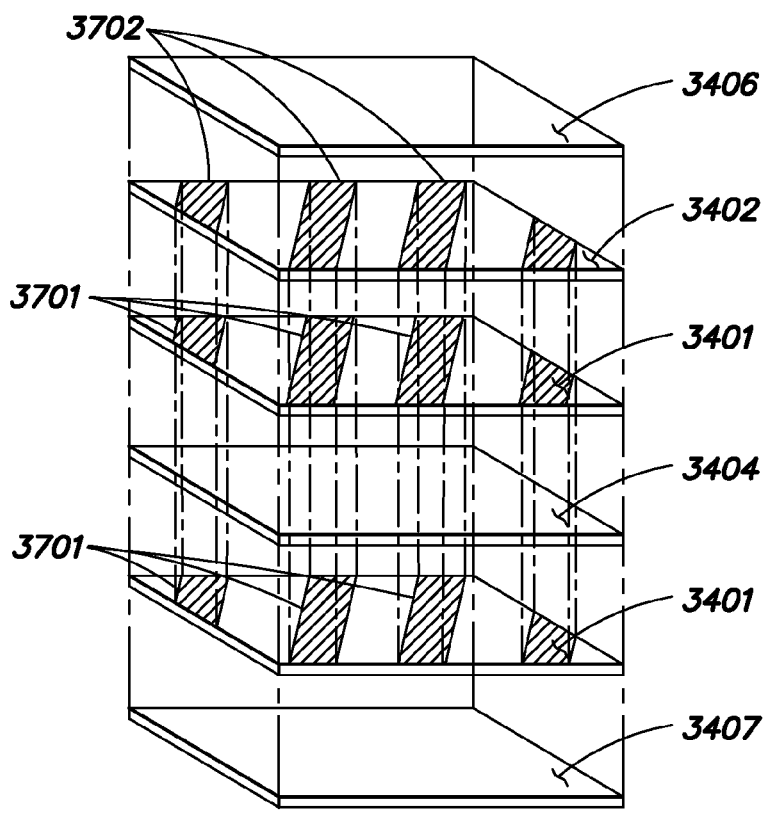
FIG. 37 is an exploded view of a radiographic plate having a radiosensitive material toward a "front side" and having toward a "back side", thereof, a radiopaque material having a pattern rendering an image exposed through the radiopaque material unusable.

According to yet another construction, as shown in FIG. 37, the mark or pattern, when the plate is exposed in an incorrect orientation, i.e. through the "back side", can be such as to cast a shadow, 3702, onto the phosphor clearly warning the reader of the radiograph that the plate was exposed from the "wrong" side. The pattern 3701 and its intensity could render such an image unreadable, necessitating repetition of the exposure in a prescribed manner, i.e., with the phosphor facing the radiation source. This construction of plate and mark or pattern would be an improvement on the current PSP technology in that it would eliminate any ambiguity as to the anatomical location of the source of the image recorded by the phosphor. Another advantage of this structure is that conventional dental film packets produce a similar result; hence, the dental profession is accustomed to such an approach. Such a disruptive label would, however, necessitate re-exposing the patient to ionizing radiation, when an exposure is improperly made, rather than simply indicating that the exposure was made from reverse side of the plate and permitting the reader to subsequently manipulate the image to have its usual orientation.

Figure 43:
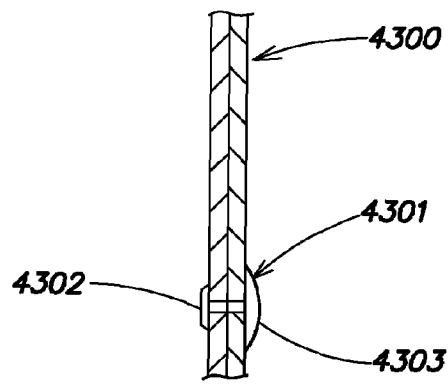
FIG. 43 is a cross-sectional view of an aspect of an embodiment of the invention using a rivet or brad to form both a "front side" marker and a "back side" marker.

According to yet another embodiment, illustrated in cross-section in FIG. 43, a small rivet, staple, brad or the like 4301, optionally holding the structure of the plate 4300 together, can serve as both a "front side" marker and a "back side" marker. Accordingly to aspects of this embodiment, the head 4302 of the rivet, staple, brad or the like 4301 can provide the "front side" marker, while the larger, spread foot 4303 of the rivet, staple, brad or the like 4301 can provide the "back side" marker. It should be understood that the roles of the head 4302 and foot 4303 of the rivet, staple, brad or the like 4301 can also be varied.

Figure 46:
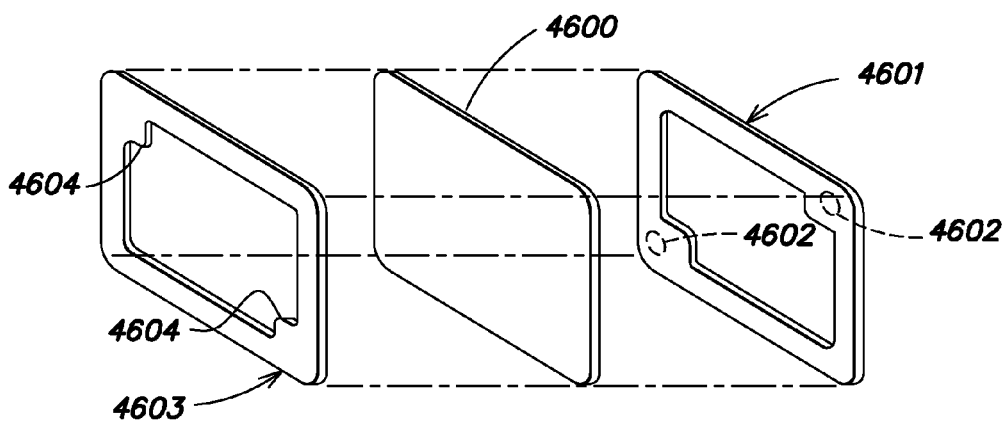
FIG. 46 is an exploded perspective view of a plate according to aspects of an embodiment of the invention including at least one frame applied to the plate.

According to yet another construction, as shown in FIG. 46, the mark or pattern-producing mass of radiopaque material 4602 can be contained or embedded within a matrix 4601 which then itself is affixed to the location on the plate 4600 chosen to demonstrate exposure from the indicated aspect of the sensitive layer in the image. As shown, the matrix can be, for example, a plastic frame 4601. The radiopaque material 4602 produces the "back side" marker, in this example. The frame 4601 can be constructed to provide compatibility with existing plate processing systems. Also, as shown, a second frame 4603 can be configures to produce a "front side" marker, as well. In this example, the "front side" marker produces an area which cannot be read because it is blocked by a portion 4604 of the frame 4603. Such matrix 4601, 4603 can be chemically bonded, solvent welded, ultrasonically welded, directly molded onto, mechanically attached, or otherwise affixed to the plate 4600 so as not to interfere with the operation of the mechanism used for converting the latent image into visible form.

Figure 50:
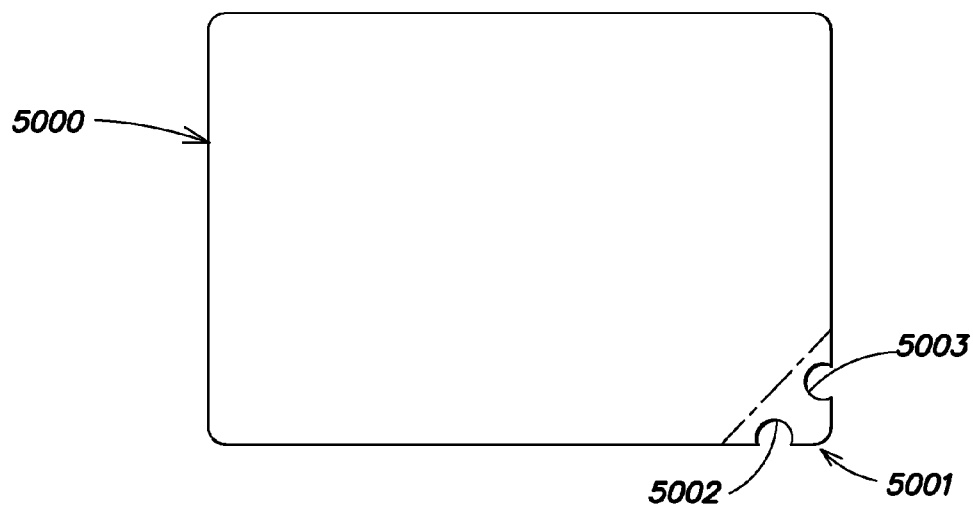
FIG. 50 is a plan view of a plate adapted to receive a corner marker feature.
Figure 51:
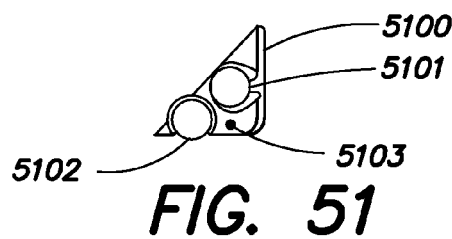
FIG. 51 is a perspective view of the corner marker feature to be received by the plate of FIG. 50.
Figure 52:
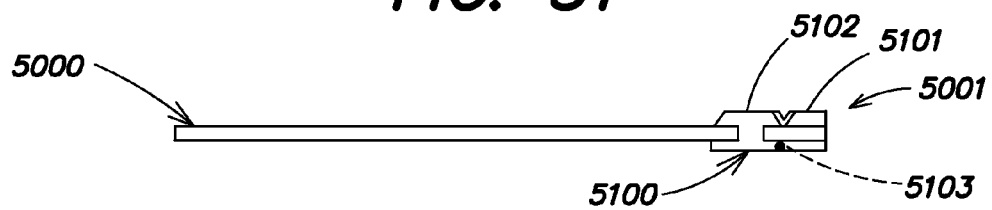
FIG. 52 is a bottom edge view of the plate of FIG. 50, including the corner marker feature of FIG. 51.

A variation on the embodiment of FIG. 46 is shown in FIGS. 50, 51 and 52. In this variation, the "frame" is not really a complete frame that surrounds the image area, but rather abbreviated to occupy only a corner (or, optionally, another small area out of the main image area) of the plate 5000. The parts of this embodiment are now described in detail.

Plate 5000 has a corner region 5001 with two voids 5002 and 5003 formed therein. The voids 5002 and 5003 are positioned, sized and shaped to retain the corner element (FIG. 51, 5100) to the plate 5000.

As shown in FIG. 51, corner element 5100 has two retaining studs 5101 and 5102, positioned, sized and shaped to fit in the voids 5002 and 5003 of plate 5000. Also, embedded within the material of which corner element 5100 is formed is a shaped body 5103 of radiopaque material. The body 5103 of radiopaque material serves the function of the "back side" marker, while the shapes of the tops of studs 5101 and 5102 serve the function of the "front side" marker.

For completeness, FIG. 52 shows the corner element 5100 attached to the plate 5000, in a bottom edge view.

Figure 53:
FIG. 53 is a plan view of a plate having a simplified marker system according to some aspects of embodiments of the invention.

According to a simplified embodiment, shown in FIG. 53, a plate 5300 has a pair of "front side" markers 5301 and a pair of "back side" markers 5302. If only the "front side" markers 5301 appear, then the resulting image indicates by the corners in which the "front side" markers appear whether it has undergone post-exposure reflection. If both the "front side" markers 5301 and the "back side" markers 5302 appear, then the resulting image was exposed from the opposite side from which it was read, i.e., it underwent pre-exposure reflection. There is insufficient information in the image, alone, to determine whether that reflection has been corrected by a subsequent post-exposure reflection. However, as described elsewhere, herein, software can replace the marks in the image with marks designed to permanently indicate the correct direction. This simplified embodiment works equally well with material that must be read only from the "front side" and material that can be read from either side.

Figure 47:
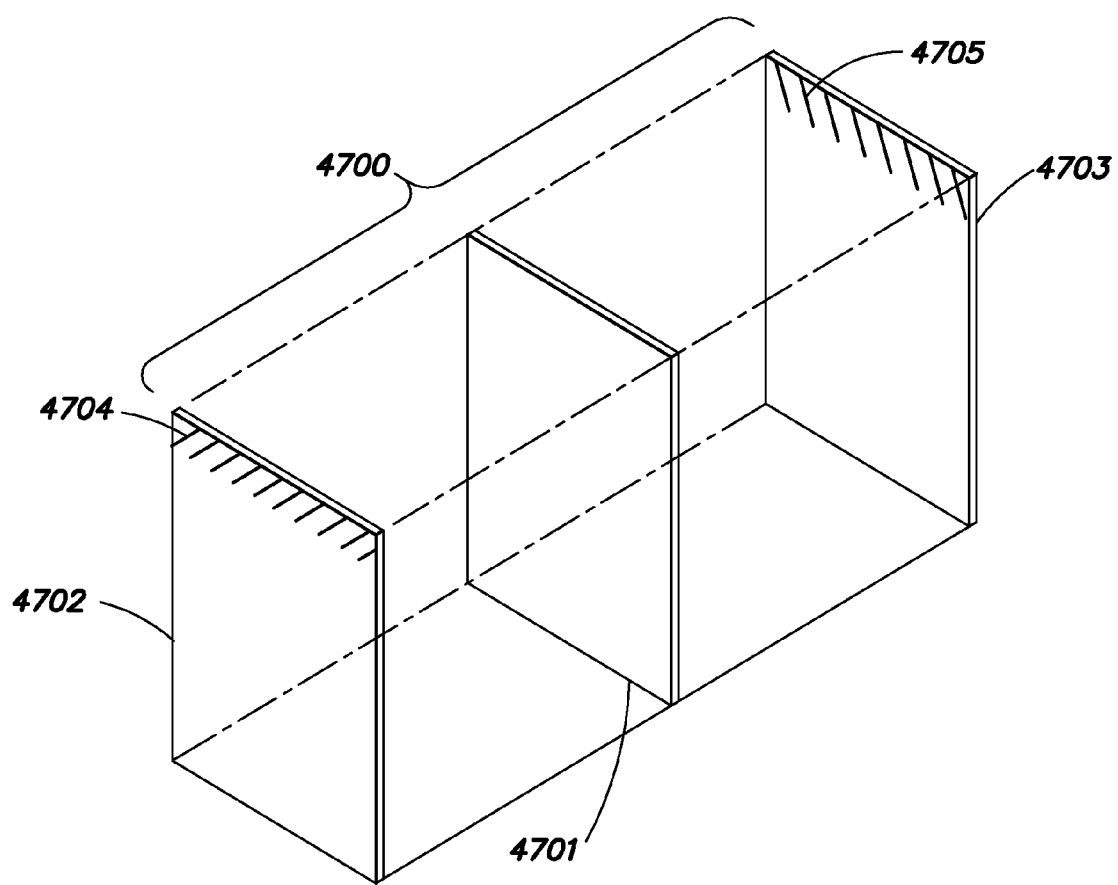
FIG. 47 is an exploded perspective view of a plate having a transparent substrate and protective layer, so that the plate can be read from either side.
Figures 48, 49:
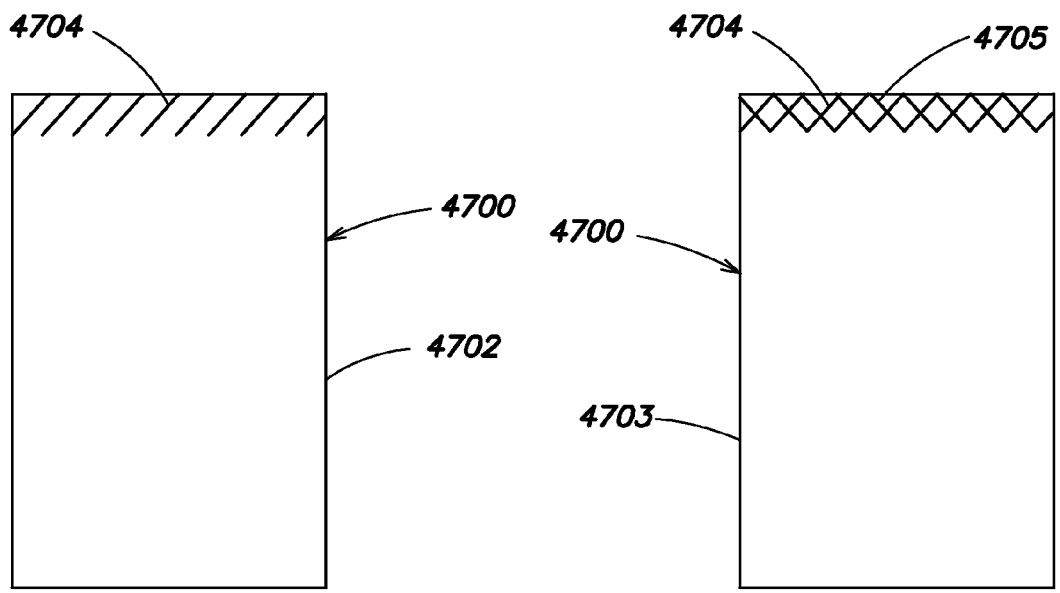
FIG. 48 is a plan view of an image produced by the plate of FIG. 47 which has been exposed from and read from the same side.
FIG. 49 is a plan view of an image produced by the plate of FIG. 47 which has been exposed from one side and read from the other side.

As shown in FIG. 47, aspects of the invention can be embodied in a plate 4700 having a phosphorescent, radiation sensitive layer 4701 and two transparent layers 4702 and 4703. One or the other of the two transparent layers 4702 and 4703 can be considered to be a substrate layer providing mechanical support for the structure, or a separate, transparent substrate layer (not shown) can be used. Transparent layers 4702 and 4703 could, in fact, be omitted, provided another substrate layer is provided, and radiopaque patterns 4704 and 4705 are provided to each side of layer 4701, for example by overprinting. Each transparent layer 4702 and 4703 should be functionally transparent to both the excitation wavelength and the phosphorescence wavelength of the radiation sensitive layer 4701. In addition to functional transparency, the layers 4702 and 4703 should exhibit low enough dispersal to be suitable for the resolution required by the application for which the plate is to be used. Each transparent layer includes at an edge a radiopaque pattern 4704 and 4705. Patterns 4704 and 4705 are selected for several qualities. They may, as in this example, be the same pattern, when each is viewed from the side of the radiation sensitive layer 4701 on which the pattern is disposed. The patterns 4704 and 4705 should be inherently asymmetrical when the plate is exposed and viewed from the same side, as shown in FIG. 48, so that a horizontal or vertical reflection of the pattern is readily apparent in the resulting image. The patterns 4704 and 4705 should combine, when exposed from one side and viewed from the other side to produce a unique pattern different from that shown in FIG. 48, as shown in FIG. 49.

When an image as shown in FIG. 48 is read from a plate, the operator can immediately discern that the image is correctly oriented. Indeed, if the image is inadvertently horizontally reflected, the pattern identifies the incorrect orientation, which can then be corrected.

When an image as shown in FIG. 49 is read from a plate, the operator (or the software performing the reading of the plate and storing of the image) can immediately discern that the image is reversed due to having been exposed from one side and read from the other. The image can then be reflected horizontally and the pattern shown in FIG. 49 can be replaced with the pattern shown in FIG. 48, thus permanently embedding in the image an indication of its correct orientation.

Combining the embodiments of FIGS. 37, 47, 48 and 49, on the side of the phosphor opposite to the one scanned, incorporate into the construction of the plate by lamination, or otherwise, a series of strips, possibly evenly spaced, possibly placed at the same distance apart as they are wide, and capable of attenuation of X-ray irradiation.

The extent of coverage of the plate with the strips might be limited to a fraction of the plate surface, e.g., along an edge, or might include the entire surface, including the entire diagnostic active area. The strips in this embodiment might be oriented to run at 45 degrees to the long and the short axis of the plate to facilitate use in scanners capable of scanning along either axis. An alternate arrangement of the strips could be perpendicular to the direction of the scan path, as governed by the scanner mount design.

The degree of attenuation might be such that the difference in the appearance of the attenuated zones and the non-attenuated zones would be below detection level of naked eye. That is to say that the shape of the repeated stripes would not be visible on visual examination of the image produced by a back side exposure, and therefore, would not degrade the diagnostic value of the image. However, a linear machine phosphorescence scan of the plate in a direction parallel to one of the axes of the plate, (not unlike the usual method currently used for reading the latent x-ray images), exposed from the back side would yield a repeating pattern, perhaps a square wave, with a period longer by a factor of $\sqrt{2}$ than the spacing of the diagonal physical strip pattern on the back side of the plate superimposed over the diagnostic image signal level. The amplitude and the wavelength of this wave would be known and its presence or absence could therefore be recognized during the processing. It might also be desirable to incorporate different spacing and width of the stripes as a machine-recognizable reference of the type or format of the plate if such is needed.

In case the pattern of the stripe shaped mark would have to be intense enough to be visible to the naked eye for technical reasons, e.g., to ensure its detection, the same square wave signal, once confirmed, could be subtracted away from the combined signal without significant deterioration of diagnostic image quality if it were to overlap it. Such can be accomplished by multiplying the pixel raw signal value within the areas affected by the mark by a factor which is a function of the extinction coefficient of the material of the marker which produced the mark and the thickness of the material of the marker, both known values.

Various aspects of embodiments of the orientation confirmation mark are next described in a sensor version.

The design of the sensor device produces the appearance of the text "correct" at the opposite edges of any image produced by exposure of this sensor. In each instance the text will be oriented so that the bottom of the letters is near the outside edge. The presence of the mark (the two instances of the text) would identify in the image the producer of the sensor regardless of software used to render the image. The software in this embodiment, on processing the image and confirming its laterality, inserts two more instances of the same text along the remaining two sides of the image. Once again the letters are oriented so that their bottoms are near the edge and their tops are toward the center of the image. When the diagnostic image is rendered using this embodiment of the invention the orientation confirmation mark consists of the four instances of the word "correct" appearing along the edges of the image allowing the viewer of the image a quick and simple confirmation of correct orientation. Should the image be rotated, the anatomical relationships are not altered and the mark still reads "correct" in the four orientations of the text. However if the diagnostic image is reflector, thus reversing the laterality of it, there will not be a single instant of "correct" which will be readable in the normal manner. The mark used might be not necessarily contain English words but clearly needs to use elements recognizable as to their correct orientation. The presence of the second set of words "correct" in this example identifies that indicates that the software processing the image used the algorithm. This embodiment of the orientation confirmation mark also confirms that the image capture device and the processing software were using the present invention methods and can state the brand of the product.

Figures 54, 55:
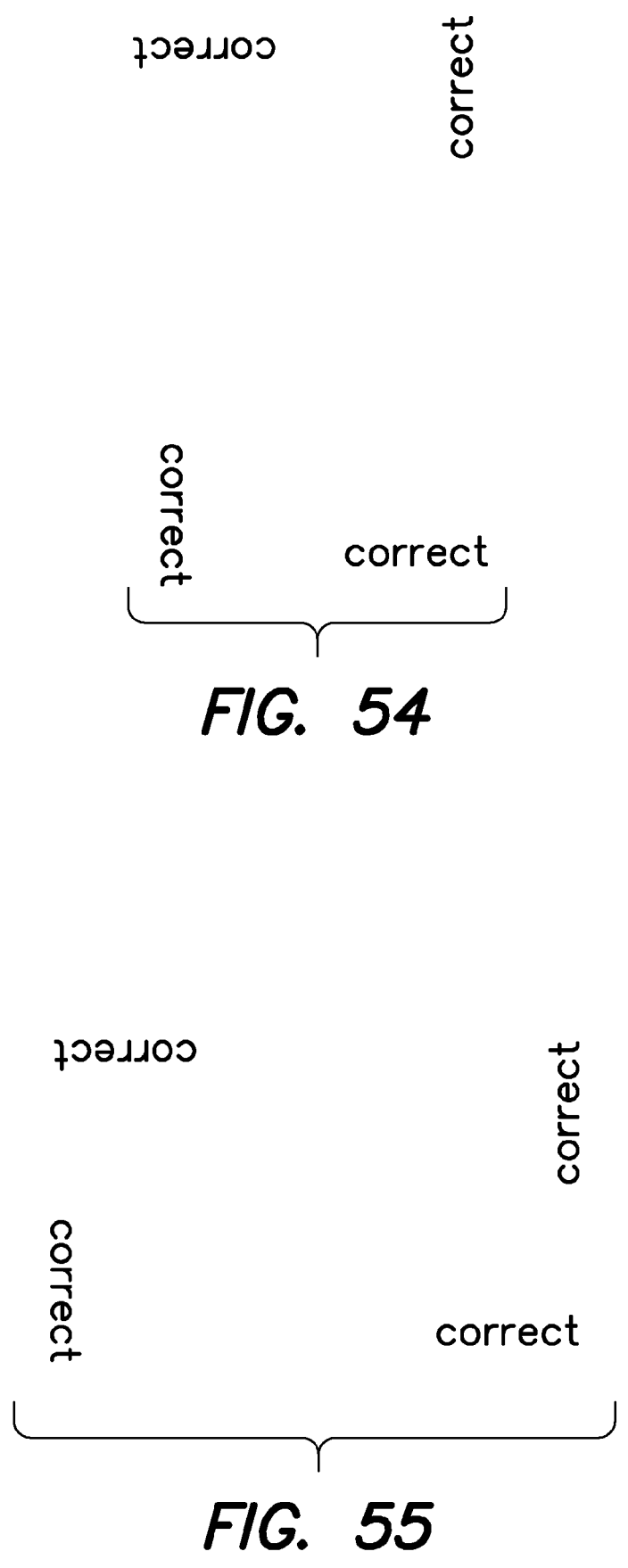
Figures 56, 57:
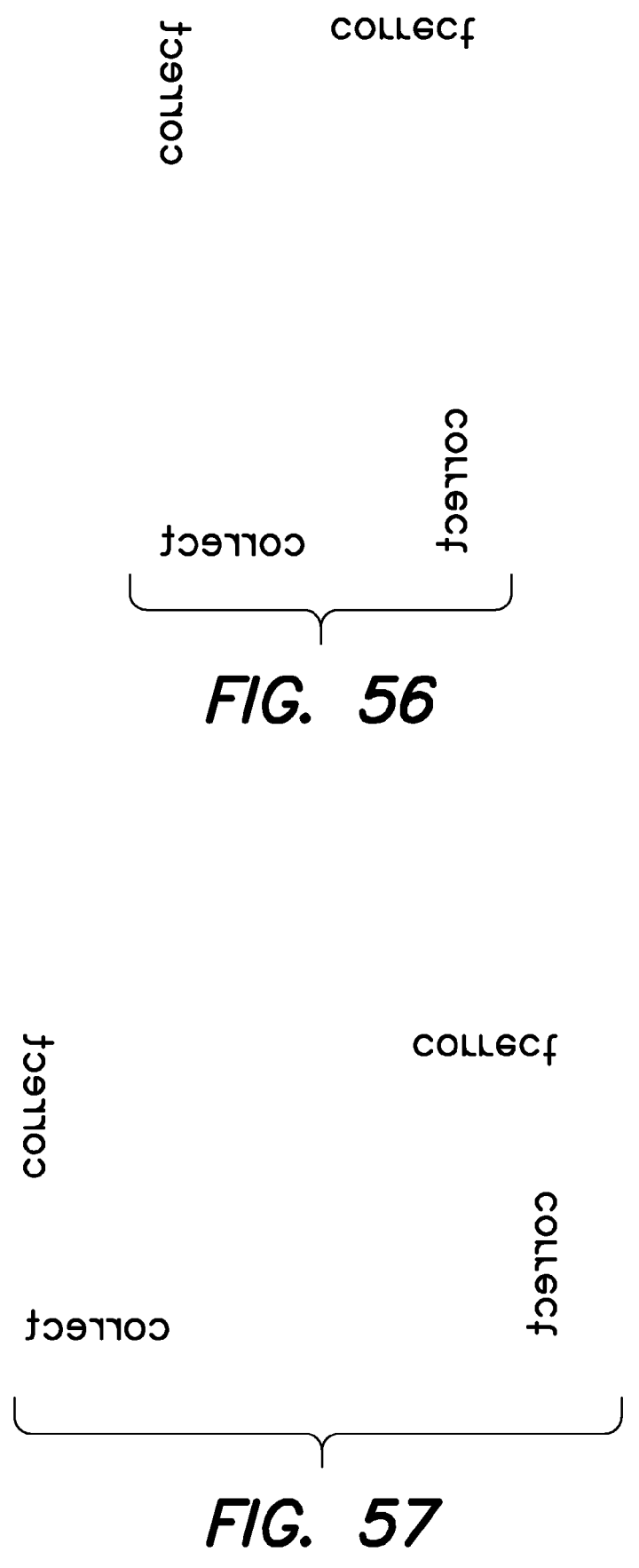

FIGS. 54-57 illustrate an exemplary embodiment of an orientation confirming mark composed of four isolated groups of characters. When properly oriented, as shown in FIG. 54, all four strings of characters are recognizable depending on viewpoint (orientation) of the observer relative to the image. Also, a 90 degree rotation as shown in FIG. 55, or its multiples do not substantially change the recognizability of the character strings composing the mark. Also note that reflection of the mark through a line, resulting in the configuration shown in FIGS. 56-57, results in a mark composed of character strings which are mirrored. These reflected strings are recognizably reversed and cannot be "read" in conventional manner no matter what the viewpoint of the observer.

Figure 58:
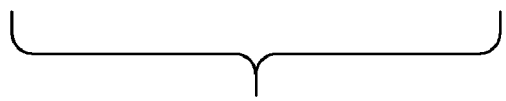
FIG. 58 is an image of a mark composed of multiple isolated single letter characters in "correct" orientation produced by a marker according to aspects of an embodiment of the invention.
Figure 59:
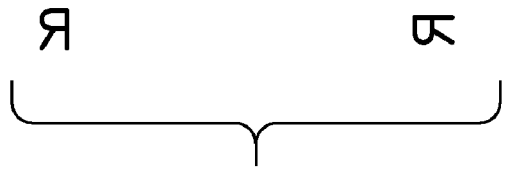
FIG. 59 is an image of a mark composed of multiple isolated single letter characters in "mirrored" orientation produced by a marker according to aspects of an embodiment of the invention.
Figure 60:
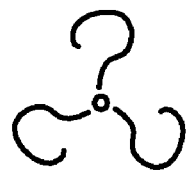
FIGS. 60, 61 and 62 are images of a mark composed of single isolated recognizable characters repeated multifold in several orientations in "correct" orientation produced by a marker according to aspects of an embodiment of the invention, which are also rotated by various amounts.
Figure 61:
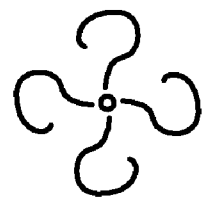
Figure 62:
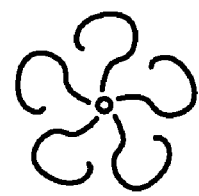
Figure 63:
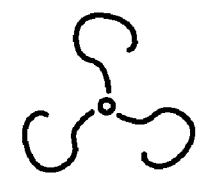
FIGS. 63, 64 and 65 are images of a mark composed of single isolated recognizable characters repeated multifold in several orientations in "mirrored" orientation produced by a marker according to aspects of an embodiment of the invention, which are also rotated by various amounts.
Figure 64:
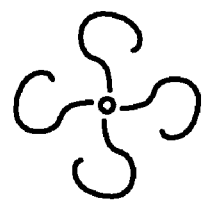
Figure 65:
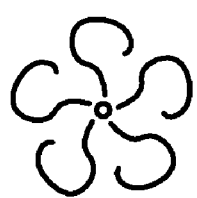
Figure 66:
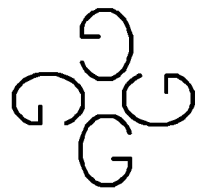
FIGS. 66, 67, 68, 69, 70, 71 and 72 are images of different marks according to various embodiments of aspects of the invention, each composed of a single recognizable character, repeated in these examples fourfold, in orientations separated by 90 degrees of rotation.
Figure 67:
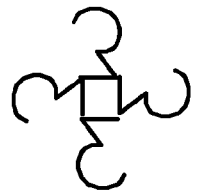
Figure 68:
Figure 69:
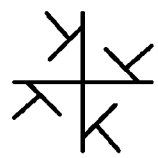
Figure 70:
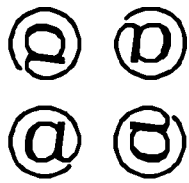
Figure 71:
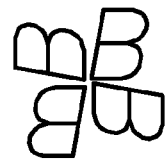
Figure 72:
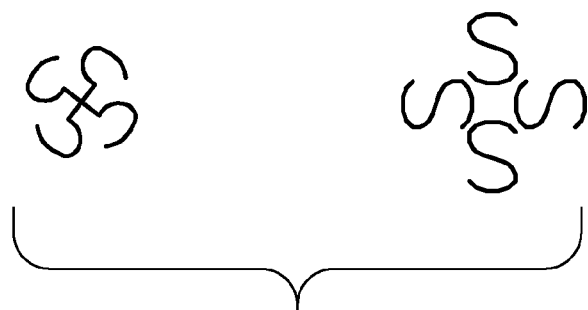
Figure 73:
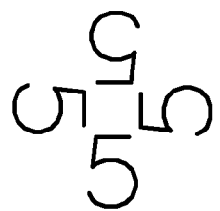
FIGS. 73, 74, 75, 76, 77, 78, 79, 80, 81 and 82 are images of different marks according to various embodiments of the invention, each composed of a single recognizable character, repeated in these examples fourfold, in orientations separated by ninety degrees of rotation.
Figure 74:
Figure 75:
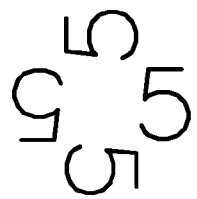
Figure 76:
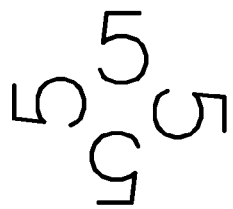
Figure 77:
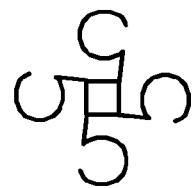
Figure 78:
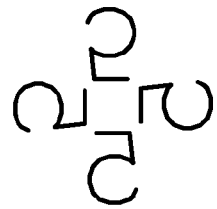
Figure 79:
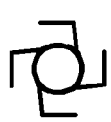
Figure 80:
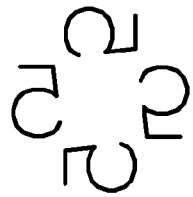
Figure 81:
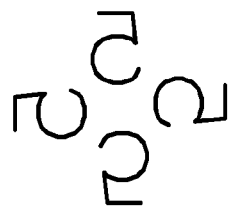
Figure 82:
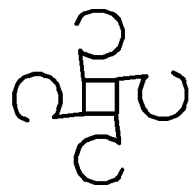

FIG. 58 shows an exemplary embodiment of an orientation confirming mark composed of isolated single letter characters. Note that the mark shown is composed of four conventionally (properly) readable letter "R" characters depending on the viewpoint (orientation) of the observer relative to the image. The reflected mark, as shown in FIG. 59, has no conventionally readable characters.

FIGS. 60-65 show exemplary embodiments of an orientation confirming mark composed of a single recognizable character repeated multifold in several orientations. Examples of threefold (120 degree), fourfold (90 degree), and fivefold (72 degree) rotational symmetry as applied to a question mark character (FIGS. 60-62), and mirror images (FIGS. 63-65) are shown. Note that the marks (FIGS. 60-62) are not identical to their mirror images (FIGS. 62-65, respectively), hence are not bilaterally symmetric. Also note that the reflected graphics do not contain a single question mark character which can be recognized as conventionally written. Also, plane rotations of the mark do not substantially change its character, i.e., reorienting images "portrait" to "landscape" and vice versa does not produce a significant change in the mark in either of its mirror image forms. The rotational symmetry properties of the mark combined with lack of bilateral symmetry produce the effect of preserving laterality orientation intact while rotation operation is performed.

FIGS. 66-72 illustrate embodiments of different orientation confirming marks, each composed of a single recognizable character, repeated in these examples fourfold, in orientations separated by ninety degrees of rotation. The characters used in these examples are letters "S", "B", "k", "a", "G", the symbol "@", and numeral "3". Also marks composed of more nearly bilaterally symmetric characters such as "3", "k", and "B" (all with a horizontal axis of symmetry) might be confused with their mirror images, and so, are less desired for some purposes. That is the mirror images contain characters which resemble the original characters within the un-reflected marks, although not in the same location. The most asymmetric characters (e.g., "G", and "a") are unlikely to be so identified in the reflected marks, and so, are more desired for some purposes.

FIGS. 73-82 illustrate embodiments of different orientation confirming marks composed of a single recognizable character, repeated in these examples fourfold, in orientations separated by ninety degrees of rotation. The character used in these examples is the numeral "5". Note that in some instances the characters are separate, in others they are conjoined, and yet in others they overlap significantly. Note that there are multiple arrangements of a single character which yield acceptable marks, as long as they preserve the asymmetric and recognizable components of the character. FIGS. 73-77 are in "correct" orientations, while FIGS. 78-82 are reflected orientations of the marks of FIGS. 73-77, respectively.

Figure 83:
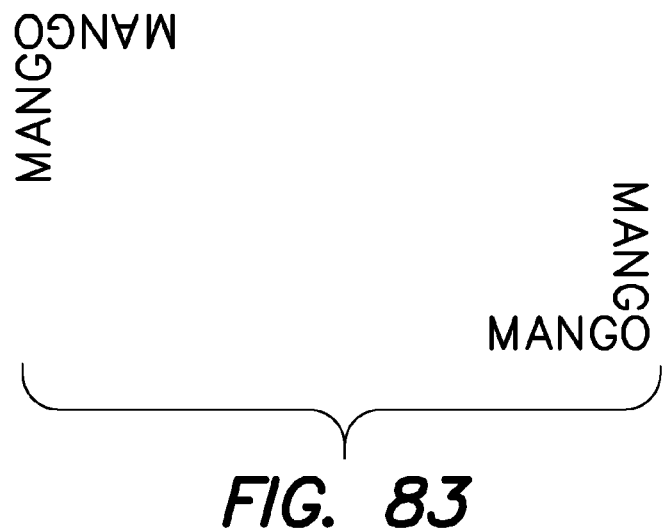
FIG. 83 is an image according to various embodiments of aspects of the invention, of a mark composed of two isolated groups of characters, in "correct" orientation.
Figure 84:
FIG. 84 is an image according to various embodiments of aspects of the invention, of a mark composed of two isolated groups of characters, in "correct" orientation, rotated 90 degrees.
Figure 84:
Figure 84:
Figure 85:
FIG. 85 is an image according to various embodiments of aspects of the invention, of a mark composed of two isolated groups of characters, in "mirrored" orientation.

FIGS. 83-85 illustrate embodiments of orientation confirming mark composed of two isolated groups of characters. The strings, however, are composed of characters which are not confined to one orientation. In the mark of FIG. 83, all four strings of characters are recognizable depending on viewpoint (orientation) of the observer relative to the image. A 90 degree rotation, as shown in FIG. 84, or its multiples do not substantially change the recognizability of the character strings composing the mark; however, reflection of the mark through a line, resulting in the mark shown in FIG. 85, results in a mark composed of character strings which are mirrored. These reflected strings are recognizably reversed and cannot be "read" in conventional manner no matter what the viewpoint of the observer.

Markers according to various aspects of embodiments of the invention described above can be made by casting low-melt temperature compositions or alloys into suitable shapes in a plate. Low temperature alloys, including eutectic alloys of Sn, Sb, Bi, Pb and/or others are suitable. Other materials and forms of material mentioned above, such as Cu, Cu foil and laminated structures for example, can also be used.

Although described in connection with intraoral dental phosphor storage plates (PSPs), it should now be evident that various aspects of embodiments of the invention can be applied to other medical and dental phosphor storage plates or films susceptible to exposure from either side, but which can only be read or scanned from one side, as well as to sensor generated images (intraoral or camera) which are exposed from one side but viewable from either one side only (printed on paper) or either side (displayed on a monitor with possibility of reflection or printed on film which can be viewed from either side). By use of the embedded confirmation mark, aspects of embodiments of the invention apply to any digital diagnostic radiographic images including photographic images, if processed and stored using any of the aspects disclosed herein or obvious to the skilled artisan in view of this disclosure. These methods and apparatus can also be used in connection with forensics or other applications where laterality and orientation are important for documentary reasons, as well as diagnostic reasons.

The third mark described herein should preferably be non-opaque with respect to the background image, so as to make it more secure.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for preserving orientation information in an image, comprising:
   reading image data from an image collecting device, including orientation information inherent to the image data; and
   embedding in the image data an orientation mark based upon the orientation information, the orientation mark unambiguously identifying when the image data is presented in a correct viewing orientation.

2. The method of claim 1, wherein collecting includes forming in the image data an exposure mark indicative of from which side of an image receptor radiation incident upon a target object was then incident upon the image receptor.

3. The method of claim 2, further comprising:
   detecting the exposure mark;
   interpreting the exposure mark; and
   determining a correspondence between the correct viewing orientation of the image data and the interpreting of the exposure mark; and wherein embedding further comprises:
   orienting the orientation mark according to the determined correspondence.

4. The method of claim 2, wherein embedding further comprises rendering the orientation mark substantially inseparable from the image data.

5. The method of claim 4, further comprising:
   including with the image data and embedded orientation mark, validation data from which a determination can be made that the embedded orientation mark and the image data are validly associated and are unaltered after embedding the orientation mark.

6. The method of claim 2, further comprising:
   removing the exposure mark from the image data.

7. The method of claim 1, wherein the orientation mark is bilaterally asymmetrical in at least two orthogonal axes.

8. The method of claim 7, wherein the orientation mark comprises at least one humanly recognizable text or punctuation character.

9. The method of claim 8, wherein the data forming the embedded orientation mark further comprises at least one humanly recognizable word.

10. The method of claim 8, wherein the text or punctuation character includes at least one numeral.

11. The method of claim 7, wherein the orientation mark comprises at least one humanly recognizable trademark.

12. The method of claim 7, wherein the orientation mark possesses radial symmetry whereby the orientation mark would remain readily recognizable when the image is rotated about a point.

13. The method of claim 7, wherein the orientation mark is similarly recognizable when the image is viewed in portrait orientation and in landscape orientation.

* * * * *